(12) United States Patent
Saito et al.

(10) Patent No.: US 11,298,271 B2
(45) Date of Patent: Apr. 12, 2022

(54) ABSORBENT ARTICLE

(71) Applicant: UNICHARM CORPORATION, Ehime (JP)

(72) Inventors: Kyota Saito, Kagawa (JP); Jirapa Changcharoen, Chachoengsao (TH); Sarinee Pichadkitjawat, Chachoengsao (TH)

(73) Assignee: UNICHARM CORPORATION, Ehime (JP)

( * ) Notice: Subject to any disclaimer, the term of this patent is extended or adjusted under 35 U.S.C. 154(b) by 519 days.

(21) Appl. No.: 16/066,311

(22) PCT Filed: Oct. 18, 2016

(86) PCT No.: PCT/JP2016/080800
§ 371 (c)(1),
(2) Date: Jun. 27, 2018

(87) PCT Pub. No.: WO2017/115529
PCT Pub. Date: Jul. 6, 2017

(65) Prior Publication Data
US 2019/0008702 A1  Jan. 10, 2019

(30) Foreign Application Priority Data

Dec. 28, 2015 (JP) .............................. JP2015-256837

(51) Int. Cl.
*A61F 13/49* (2006.01)
*A61F 13/496* (2006.01)
*A61F 13/56* (2006.01)

(52) U.S. Cl.
CPC ........ *A61F 13/49011* (2013.01); *A61F 13/49* (2013.01); *A61F 13/496* (2013.01); *A61F 13/56* (2013.01); *A61F 13/565* (2013.01)

(58) Field of Classification Search
CPC .. A61F 13/49; A61F 13/49011; A61F 13/496; A61F 13/56; A61F 13/565;
(Continued)

(56) References Cited

U.S. PATENT DOCUMENTS 2,290,110 A    7/1942   McGraw
5,368,585 A   11/1994   Dokken
(Continued)

FOREIGN PATENT DOCUMENTS

CN         101641066 A    2/2010
DE    202006003740 U1    7/2006
(Continued)

OTHER PUBLICATIONS

Office Action in EA Application No. 201891180, dated Jan. 28, 2020, 2pp.
(Continued)

*Primary Examiner* — Michele M Kidwell
(74) *Attorney, Agent, or Firm* — Hauptman Ham, LLP

(57) ABSTRACT

An absorbent article including a front waist portion, a back waist portion, and a crotch portion. An end portion of the back waist portion on an other side in the lateral direction is joined by a second joining portion to a fastening member, and the fastening member has a fastening portion being capable of being fastened to the front waist portion when putting on the absorbent article. While the front waist portion and the back waist portion are being stretched in the lateral direction, the lateral distance of the front waist portion from the lateral center of the absorbent main body to a lateral end of the front waist portion on the other side is smaller than the lateral distance of the back waist portion from the lateral center of absorbent main body to a lateral end of the back waist portion on the other side.

10 Claims, 11 Drawing Sheets

(58) Field of Classification Search
CPC .......... A61F 13/5666; A61F 2013/5688; A61F 13/5655; A61F 13/4963; A61F 13/581; A61F 2013/588
See application file for complete search history.

(56) References Cited

U.S. PATENT DOCUMENTS

| | | | | |
|---|---|---|---|---|
| 5,370,634 | A * | 12/1994 | Ando | A61F 13/49009 604/358 |
| 5,695,488 | A * | 12/1997 | Sosalla | A61F 13/5633 604/385.24 |
| 6,454,752 | B1 * | 9/2002 | Huang | A61F 13/15756 604/385.01 |
| 8,211,077 | B2 * | 7/2012 | Sugiyama | A61F 13/5655 604/385.29 |
| 8,679,085 | B2 * | 3/2014 | Ronstrom | A61F 13/505 604/398 |
| 10,327,961 | B2 * | 6/2019 | Saito | A61F 13/5655 |
| 2011/0066127 | A1 | 3/2011 | Kuwano et al. | |
| 2012/0209237 | A1 * | 8/2012 | Paz | A61F 13/70 604/392 |
| 2019/0008703 | A1 * | 1/2019 | Saito | A61F 13/56 |
| 2019/0008706 | A1 * | 1/2019 | Saito | A61F 13/5638 |
| 2019/0029898 | A1 * | 1/2019 | Ostertag | A61F 13/49014 |

FOREIGN PATENT DOCUMENTS

| | | |
|---|---|---|
| JP | H4-5826 U | 1/1992 |
| JP | H663077 A | 3/1994 |
| JP | 2008-104874 A | 5/2008 |
| JP | 201210904 A | 1/2012 |
| WO | 2014/208781 A2 | 12/2014 |

OTHER PUBLICATIONS

Office Action in JP Application No. 2015-256837, dated Jul. 3, 2018, 7pp.
Office Action in CN Application No. 201680076715.2, dated Aug. 3, 2020, 17pp.
International Preliminary Report on Patentability in PCT Application No. PCT/JP2016/080800, dated Nov. 29, 2016, 17pp.
Extended European Search Report in EP Application No. 16881509.0, dated Nov. 22, 2018, 6pp.
Office Action in BR Application No. 112018012431-1, dated May 14, 2020, 4pp.
International Search Report for PCT/JP2016/080800, dated Nov. 29, 2016, 2 pages.
Office Action in TW Application No. 105140672, dated Jun. 29, 2020, 20pp.
Office Action in CN Application No. 201680076715.2, dated Jan. 6, 2021, 15pp.
Office Action in TW Application No. 105140672, dated Sep. 29, 2020, 7pp.
Office Action in AU Application No. 2016381718, dated Oct. 23, 2020, 4pp.
Office Action in CN Application No. 201680076715.2, dated Jun. 22, 2021, 12pp.
Office Action in IN Application No. 201817023930, dated Sep. 22, 2021, 8pp.

* cited by examiner

ABSORBENT ARTICLE

RELATED APPLICATIONS

The present application is a National Phase of International Application Number PCT/JP2016/080800, filed Oct. 18, 2016, and claims priority to Japanese Application Number 2015-256837, filed Dec. 28, 2015.

TECHNICAL FIELD

The present invention relates to an absorbent article.

BACKGROUND ART

As an conventional absorbent article including an absorbent body that absorbs liquid such as excrement, there is provided, for example in PTL 1, a so-called half-open underpants-shaped diaper in which the side of a front waist portion and the side of a back waist portion are joined on a one side in the lateral direction and in which the front waist portion and the back waist portion are not joined on an other side in the width direction.

This half-open underpants-shaped diaper, in which the front waist portion and the back waist portion are not joined on the other side (the open side), has a fastening portion (a tape fastener) projected from a lateral other-side end portion of the back waist portion, the fastening portion being fastened to the front waist portion.

CITATION LIST

Patent Literature

[PTL 1] Japanese Unexamined Utility Model Application Publication No. H4-5826

SUMMARY OF INVENTION

Technical Problem

However, as in a half-open underpants-shaped diaper disclosed in PTL 1, assuming that the lateral distance of the front waist portion from an end of the front waist portion on the other side in the lateral direction to the lateral center of a crotch portion (a portion placed under the wearer's crotch; an absorbent body is provided therein) is equal to the lateral distance of the back waist portion from an end of the back waist portion on the other side in the lateral direction to the lateral center of the crotch portion. In this case, when fastening a fastening portion to the front waist portion, enlarged is a stacking region in which the other-side end portion of the front waist portion is not stacked and fixed to other-side end portion of the back waist portion. This makes it more likely to cause positional shift in the stacking region of the other-side end portions of the front and back waist portions when a baby (a wearer) wriggles his/her legs or rolls over. Also, when positional shift occurs, the magnitude thereof will increase.

The present invention was achieved in light of the problems described above, and an aspect of the present invention is to suppress positional shift on the open side of a half-open underpants-shaped diaper, achieving good fit of the diaper.

Solution to Problem

An aspect of the invention to achieve the above advantage is an absorbent article having a longitudinal direction, a lateral direction intersecting the longitudinal direction, and a front-back direction intersecting the longitudinal direction and the lateral direction, the absorbent article including: a front waist portion extending along the lateral direction; a back waist portion extending along the lateral direction; and a crotch portion provided between the front waist portion and the back waist portion, the front waist portion and the back waist portion each including an elastic region extending along the lateral direction, a one-side end portion of the back waist portion on a one side in the lateral direction being joined by a first joining portion to a one-side end portion of the front waist portion on the one side in the lateral direction, an other-side end portion of the back waist portion on an other side in the lateral direction being joined by a second joining portion to a fastening member, the fastening member having a fastening portion being capable of being fastened to the front waist portion when putting on the absorbent article, while the front waist portion and the back waist portion being stretched in the lateral direction, a lateral distance of the front waist portion from a lateral center of the crotch portion to an other-side end of the front waist portion is smaller than a lateral distance of the back waist portion from the lateral center of the crotch portion to an other-side end of the back waist portion.

Other features of the present invention will become apparent from the description of the present specification and the accompanying drawings.

Advantageous Effects of Invention

According to the invention, in a half-open underpants-shaped diaper, it is possible to suppress positional shift on its open side, making it possible to achieve good fit of the diaper.

BRIEF DESCRIPTION OF DRAWINGS

FIG. 5A is a diagram showing a manner in which a diaper is used, FIG. 5B is a side view of a diaper when it is put on, and FIG. 5C is a front view of a diaper when it is put on.

FIG. 6 is a diagram illustrating a state where a diaper according to the modified example is put on.

FIG. 7A is a schematic plan view showing an example of the range of a target region and the position of a fastening portion when a diaper is put on.

FIG. 8 is a schematic plan view showing a modified example 1 of the range of the target region and the position of a fastening portion when a diaper is put on.

DESCRIPTION OF EMBODIMENTS

Figure 1:
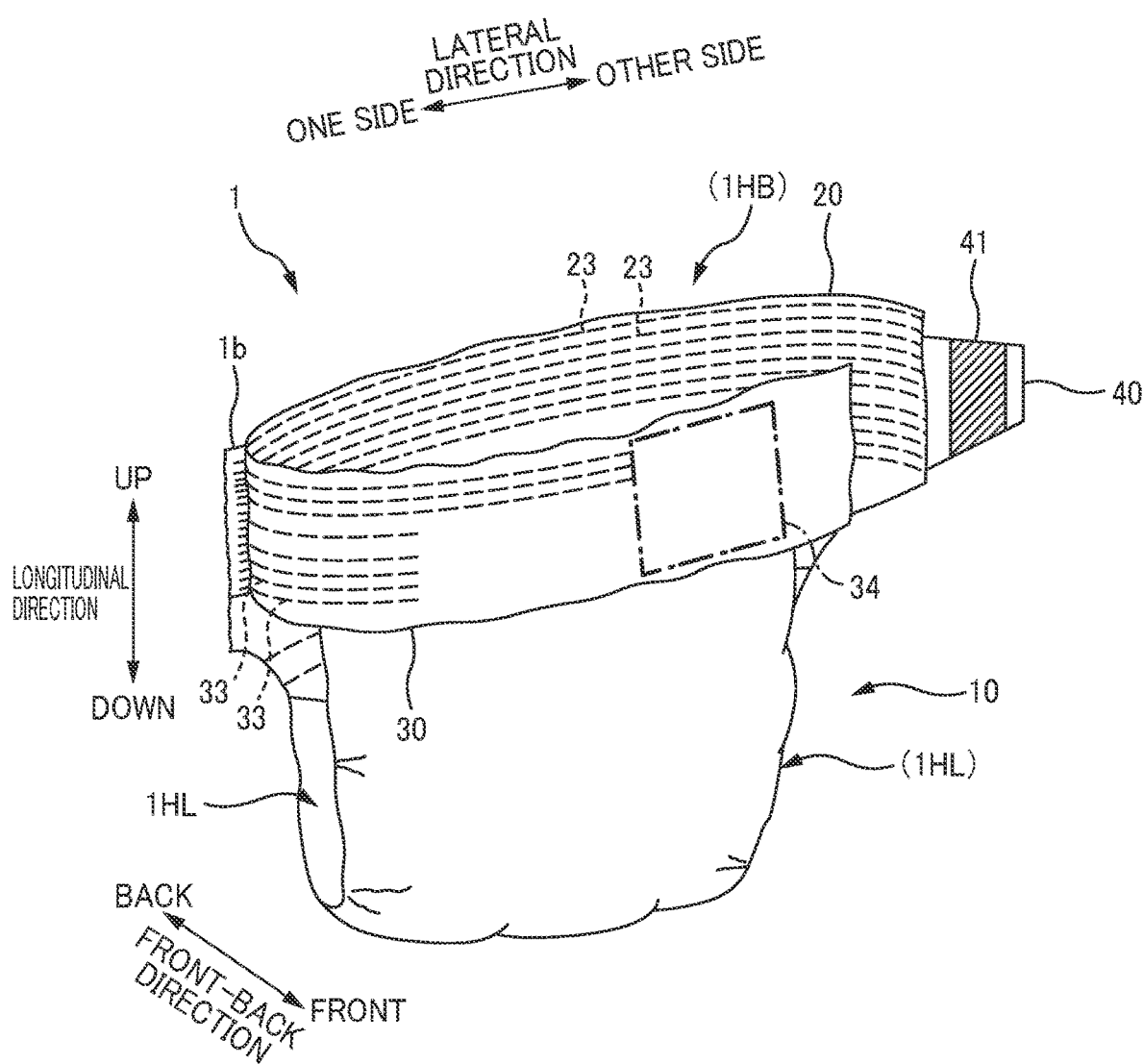
FIG. 1 is a schematic perspective view showing an example of a diaper according to an embodiment of the invention.

At least the following matters will be made clear by the description in the present specification and the accompanying drawings.

An absorbent article having a longitudinal direction, a lateral direction intersecting the longitudinal direction, and a front-back direction intersecting the longitudinal direction and the lateral direction, the absorbent article including: a front waist portion extending along the lateral direction; a back waist portion extending along the lateral direction; and a crotch portion provided between the front waist portion and the back waist portion, the front waist portion and the back waist portion each including an elastic region extending along the lateral direction, a one-side end portion of the back waist portion on a one side in the lateral direction being joined by a first joining portion to a one-side end portion of the front waist portion on the one side in the lateral direction, an other-side end portion of the back waist portion on an other side in the lateral direction being joined by a second joining portion to a fastening member, the fastening member having a fastening portion being capable of being fastened to the front waist portion when putting on the absorbent article, while the front waist portion and the back waist portion being stretched in the lateral direction, a lateral distance of the front waist portion from a lateral center of the crotch portion to an other-side end of the front waist portion is smaller than a lateral distance of the back waist portion from the lateral center of the crotch portion to an other-side end of the back waist portion.

With such an absorbent article, the lateral distance from the lateral center of the crotch portion to the other-side end of the front waist portion is smaller than a lateral distance from the lateral center of the crotch portion to the other-side end of the back waist portion (an end on the second joining portion side). This makes smaller a stacking region of the back waist portion on the laterally other side on which the lateral other-side end portion of the front waist portion is stacked when putting on the absorbent article. This makes positional shift in the stacking part less likely to occur, and even if the positional shift occurs, it is possible to reduce the shift. This makes it possible to achieve good fit of the absorbent article when putting on the diaper.

In such an absorbent article, it is desirable that while the front waist portion and the back waist portion being stretched in the lateral direction, the lateral distance of the front waist portion from the lateral center of the crotch portion to the other-side end of the front waist portion is larger than a lateral length of the fastening member.

With such an absorbent article, while the fastening portion being fastened to the front waist portion so that a lateral tip end of the fastening member (an end opposite to the second joining portion) is positioned on the lateral center of the crotch portion, the second joining portion is placed on the other-side end portion of the front waist portion. And, the second joining portion having a high rigidity does not come into direct contact with wearer's skin. This makes touch better.

In such an absorbent article, it is desirable
that the elastic region of the back waist portion is arranged in the other-side end portion of the back waist portion on the other side in the lateral direction, and
that, while the fastening portion being fastened to the front waist portion so that an end of the fastening portion on a side closer to the second joining portion is positioned in the lateral direction on an end of the crotch portion opposite to the first joining portion,
the elastic region arranged in the other-side end portion of the back waist portion is located on the non-skin side of an other-side end portion of the front waist portion on an other side in the lateral direction, and
the elastic region arranged in the other-side end portion of the back waist portion has a stacking part in which the elastic region is stacked on the other-side end portion of the front waist portion.

With such an absorbent article, when the absorbent article is put on, the elastic region arranged in the other-side end portion of the back waist portion on the other side in the lateral direction is located on the non-skin side of the other-side end portion of the front waist portion on the other side in the lateral direction. And, the elastic region and the other-side end portion of the front waist portion are stacked (in the thickness direction). Accordingly, the other-side end portion of the front waist portion is pressed against the wearer's skin with elastic force. This suppresses positional shift of the other-side end portion of the front waist portion, making it possible to further improve the fit of the absorbent article when the absorbent article is put on.

In such an absorbent article, it is desirable that the other-side end portion of the front waist portion does not have stretchability.

With such an absorbent article, the other-side end portion of the front waist portion does not have stretchability. Accordingly, the end portion can be pressed against the wearer's skin in a surface-to-surface contact manner with the elastic force of the elastic region of the back waist portion. This improves touch, making it possible to further improve the fit of the absorbent article.

In such an absorbent article, it is desirable that while the fastening portion being fastened to the front waist portion so that the end of the fastening portion on the side closer to the second joining portion is positioned in the lateral direction on the end of the crotch portion opposite to the first joining portion, a longitudinal length of the elastic region arranged in the other-side end portion of the back waist portion is larger than a longitudinal length of the other-side end portion of the front waist portion.

With such an absorbent article, the elastic region arranged in the other-side end portion of the back waist portion covers the other-side end portion of the front waist portion. Consequently, elastic force is exerted on the entirety of the other-side end portion of the front waist portion, making it possible to further suppress positional shift of the other-side end portion of the front waist portion.

In such an absorbent article, it is desirable that while the fastening portion being fastened to the front waist portion so that an end of the fastening portion on a side closer to the second joining portion is positioned in the lateral direction on an end of the crotch portion opposite to the first joining portion, the second joining portion is located on a front side relative to the first joining portion.

With such an absorbent article, the second joining portion is located on the front side (stomach side) relative to the first joining portion when putting on the absorbent article. The second joining portion having a rigidity serves as a support to suppress downward positional shift. This suppresses downward positional shift caused by the protrusion of the wearer's stomach, making the fit better.

In such an absorbent article, it is desirable that a rigidity of the second joining portion is larger than a rigidity of the front waist portion.

With such an absorbent article, the rigidity of the second joining portion is larger than the rigidity of the front waist portion. This further ensures support for downward positional shift of the front waist portion, further suppressing downward positional shift caused by the protrusion of the wearer's stomach.

In such an absorbent article, it is desirable that a number of components stacked in the second joining portion is larger than a number of components stacked in the front waist portion.

With such an absorbent article, the number of components stacked in the second joining portion is larger than the number of components stacked in the front waist portion. This make larger the rigidity of the second joining portion than the rigidity of the front waist portion, making it possible to further ensure support for downward positional shift without taking a measure such as replacing with thicker members.

Embodiment

The following describes a half-open underpants-shaped disposable diaper 1 (hereinafter also merely referred to as a diaper 1) as an example of an absorbent article according to the present embodiment.

Configuration of Diaper 1

The configuration of the diaper 1 will be described below with reference to FIGS. 1 to 4.

Figure 2:
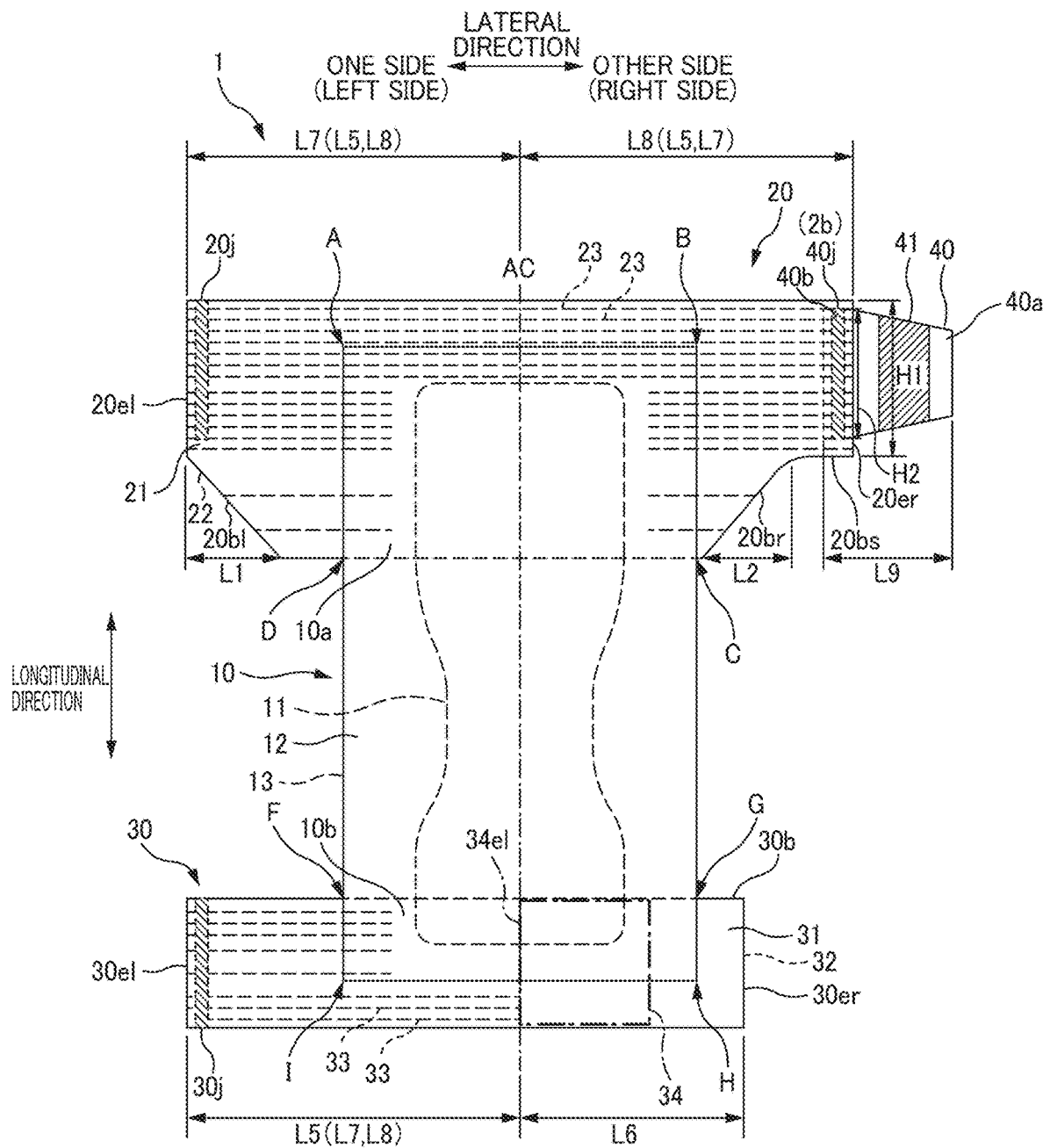
FIG. 2 is a schematic plan view of a diaper in an unfolded state as viewed from the skin side of a wearer.
Figure 3:
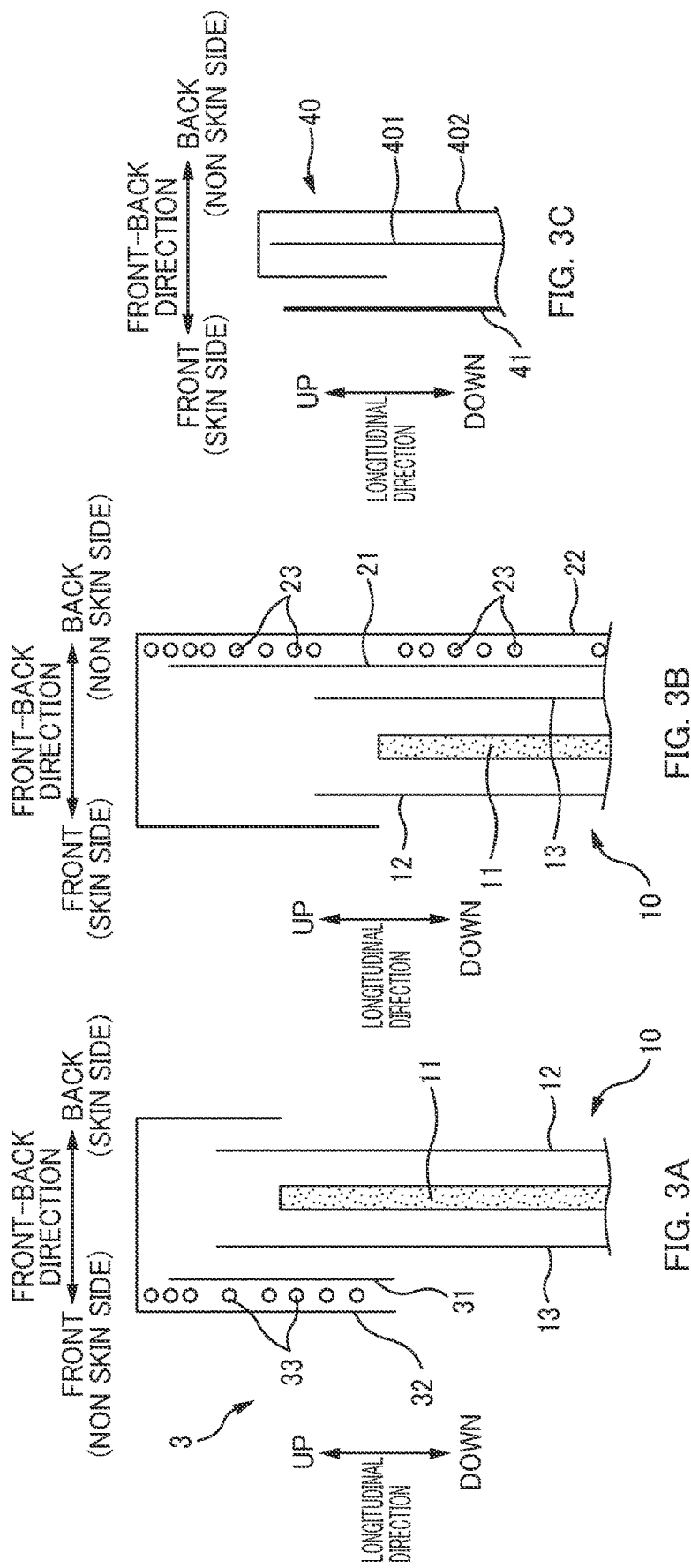
FIG. 3A is a schematic cross-sectional view of a front waist portion.
FIG. 3B is a schematic cross-sectional view of a back waist portion.
FIG. 3C is a schematic cross-sectional view of a fastening member.
Figure 4:
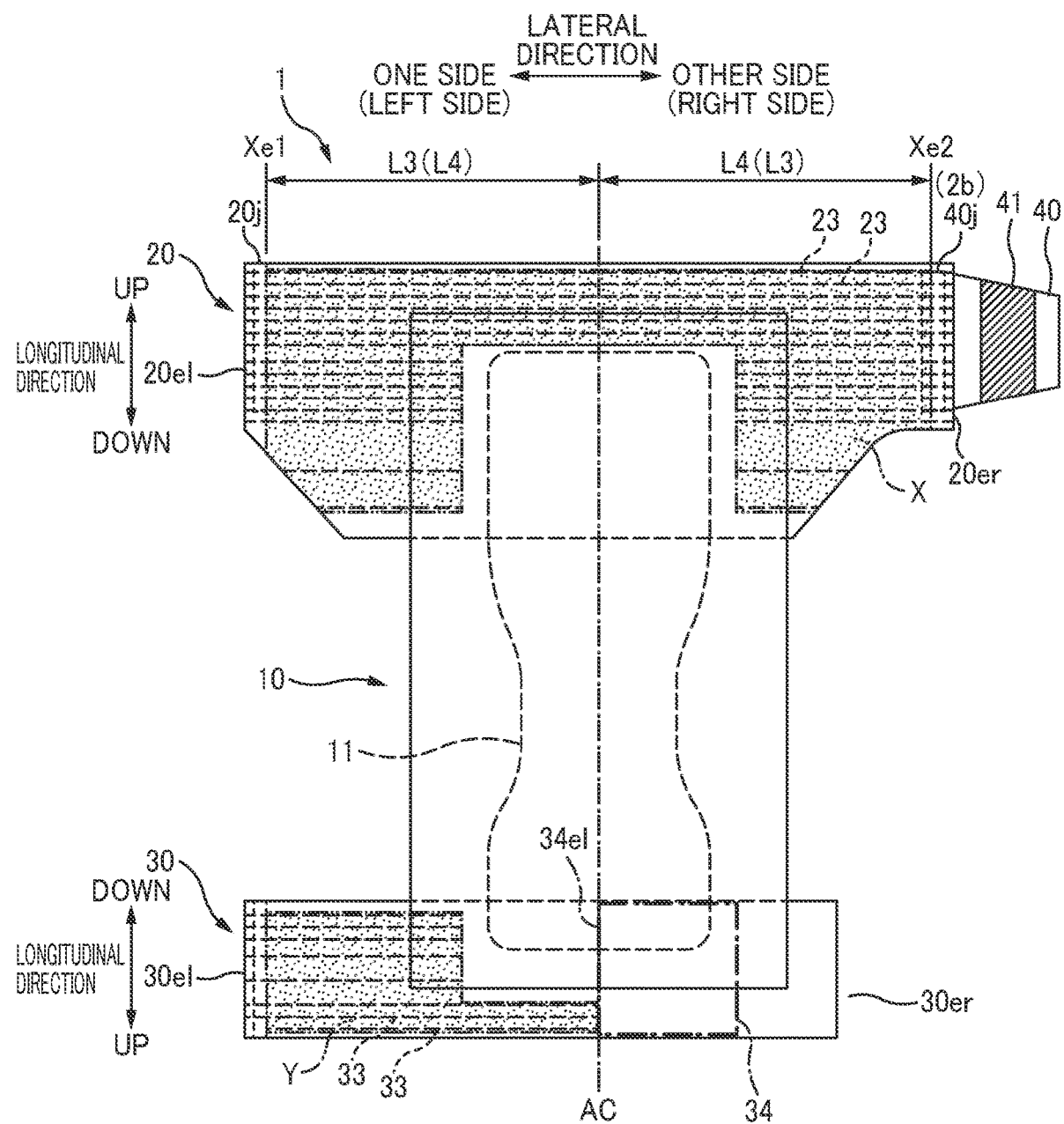
FIG. 4 is a diagram illustrating elastic regions X and Y.
Figure 5:
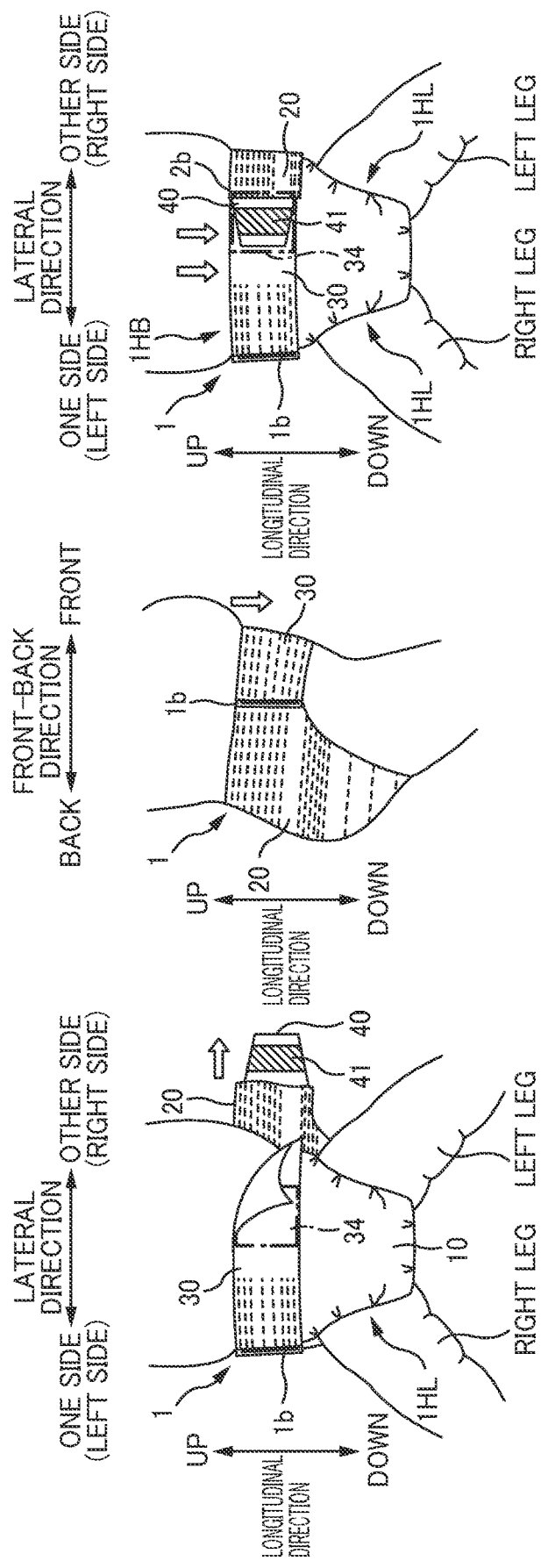

FIG. 1 is a schematic perspective view showing an example of a diaper 1 according to the present embodiment. FIG. 2 is a schematic plan view of a diaper 1 in an unfolded state as viewed from the skin side of a wearer. FIG. 3A is a schematic cross-sectional view of a front waist portion 30, FIG. 3B is a schematic cross-sectional view of a back waist portion 20, and FIG. 3C is a schematic cross-sectional view of a fastening member 40. FIG. 4 is a diagram illustrating elastic regions X and Y.

The diaper 1 is a disposable diaper mainly for use of newborn infants, infants, or the like. As shown in FIG. 1, the diaper 1 has a "longitudinal direction", a "lateral direction" that intersects the longitudinal direction, and a "front-back direction" that intersects the longitudinal direction and the lateral direction. In the longitudinal direction, a side of a wearer's waist is defined as a "up" side, and a side of a wearer's crotch is defined as a "down" side. In the front-back direction, a side of a wearer's stomach is defined as a "front" side, and a side of a wearer's back is defined as a "back" side. When a wearer puts on a diaper 1, a side being in contact with wearer's skin is defined as a "skin side", and the side opposite thereto is defined as a "non-skin side". Also, in the description below, the left side in the lateral direction in the drawings is the "one side", and the right side is the "other side" (see FIGS. 2 and 4).

The diaper 1 includes: an absorbent main body 10 (also called a "crotch portion") that is arranged at the crotch of the wearer and absorbs excrement; a back waist portion 20 that covers the back side of the wearer; and a front waist portion 30 that covers the stomach side of the wearer. In an end portion of the back waist portion 20 on the other side, the fastening member 40 is provided projecting laterally, and the fastening member 40 includes a fastening portion 41 which can be fastened to the front waist portion 30 when putting on the diaper 1.

The diaper 1 in the unfolded state shown in FIG. 2 is folded in half with an approximately central position in the longitudinal direction serving as the folding position, and end portions of the back waist portion 20 and the front waist portion 30 on a one side in the lateral direction are joined together in the first joining portion 1b, thus forming a leg opening 1HL on the one side. The end portions of the back waist portion 20 and the front waist portion 30 on the other side in the lateral direction are not joined together, and a leg opening 1HL on the other side and a waist opening 1HB are formed by fastening the fastening portion 41 to the front waist portion 30.

In other words, the diaper 1 of the present embodiment is a so-called "half-open diaper" in which the back waist portion 20 and the front waist portion 30 are joined and closed on the one side in the lateral direction, and are unjoined and open on the other side. Hereinafter, a side on which the back waist portion 20 and the front waist portion 30 are unjoined and open (the other side in the lateral direction) is also referred to as an "open side".

The back waist portion 20 and the front waist portion 30 have an approximately rectangular planar shape. The back waist portion 20 is fixed to one lengthwise end portion 10a of the absorbent main body 10, and the front waist portion 30 is fixed to an other lengthwise end portion 10b. That is, the back waist portion 20 and the front waist portion 30 are bridged by the absorbent main body 10, and are parallel with a space between each other in the lengthwise direction of the absorbent main body 10.

The one lengthwise end portion 10a of the absorbent main body 10 is a region in which the absorbent main body 10 and the back waist portion 20 are stacked (a first region), and in FIG. 2, a rectangular region surrounded by lines A-B-C-D. The other lengthwise end portion 10b of the absorbent main body 10 is a region in which the absorbent main body 10 and the front waist portion 30 are stacked (a second region), and in FIG. 2, a rectangular region surrounded by lines F-G-H-I.

Absorbent Main Body 10

The absorbent main body 10 (a crotch portion) is approximately shaped as an elongated rectangle in a plan view, and is arranged at a central position in the lateral direction, with its lengthwise direction extending along the longitudinal direction of the diaper 1. In FIGS. 2 and 4, a center line AC (indicated by a single dotted/dashed line) is the center of the absorbent main body 10 in the lateral direction.

The absorbent main body 10 includes: an absorbent body 11 that absorbs and holds a liquid; a liquid-permeable top face sheet 12 that covers the absorbent body 11 on the wearer's skin side and allows the passage of excrement such as urine; and a liquid-impermeable back face sheet 13 that covers the absorbent body 11 on the non-skin side and prevents the leakage of a liquid from the non-skin side. The absorbent body 11 is constituted by liquid-absorbent fibers such as pulp fibers and is formed with a predetermined shape such as approximately an hourglass shape in a plan view as shown in FIG. 2, and has a superabsorbent polymer incorporated therein.

In order to prevent side leakage and to improve a fit around legs, leg gathers LG (leg elastic portions) that stretch and contract along the lengthwise direction of the absorbent main body 10 are provided at locations on respective side portions in the lateral direction of the absorbent main body 10. But, for convenience, they are omitted in FIG. 2 or the like.

Back Waist Portion 20

The back waist portion 20, as shown in FIG. 3B, includes: a skin-side member 21 that is located on the wearer's skin side; a non-skin-side member 22 that is located on the non-skin side; and a plurality of elastic strings 23 that are located between the skin-side member 21 and the non-skin-side member 22. The non-skin-side member 22 has an upper end portion which is folded back toward the skin side, and the upper end portion wraps the upper end portion of the skin-side member 21 and the upper end portion of the absorbent main body 10.

The skin-side member 21 and the non-skin-side member 22 are each a flexible sheet member that is constituted by a nonwoven fabric or the like. The elastic strings 23 are elastic members that give the back waist portion 20 lateral stretchability. In the present embodiment, a plurality of the elastic strings 23 are arranged side-by-side at a predetermined longitudinal interval. And the elastic strings 23 are joined with an adhesive between the skin-side member 21 and the non-skin-side member 22 with being stretched in the lateral direction.

The back waist portion 20 has a first joining region 20*j* in its end portion on the one side, and the first joining region 20*j* is joined to a joining region 30*j* (to be described later) of the front waist portion 30 by certain joining means (e.g., heat welding or ultrasonic welding), forming the first joining portion 1*b* of the diaper 1. The back waist portion 20 has a second joining region 40*j* in in its end portion on the other side, and the second joining region 40*j* is joined to the fastening member 40.

In the lower end portion of the back waist portion 20, an inclined portion 20*bl* that is inclined obliquely downward from the lateral end 20*el* on the lateral one side toward laterally inside (the side at which the absorbent main body 10 is located) is provided on the lateral one side. Also, in the lower end portion of the back waist portion 20, the following portion are provided on the lateral other side: a straight portion 20*bs* being substantially parallel with the lower end 30*b* of the front waist portion 30 and extending from the lateral end 20*er* on the lateral other side toward laterally inside; and an inclined portion 20*br* that is inclined obliquely downward from the straight portion 20*bs* toward laterally inside. The inclined portion 20*bl* on the lateral one side and the inclined portion 20*br* on the lateral other side are symmetrical with each other about the lateral, center line AC of the absorbent main body 10.

Due to the back waist portion 20 having the straight portion 20*bs* which is substantially parallel with the lower end 30*b* of the front waist portion 30 as mentioned above, when the diaper 1 is put on by fastening the fastening portion 41 to the front waist portion 30, the lower end 30*b* of the front waist portion 30 can be aligned with the straight portion 20*bs* of the back waist portion 20. This makes better the appearance of the diaper 1 while being put on. By making the lateral length L2 of the inclined portion 20*br* on the lateral other side larger than the lateral length L1 of the inclined portion 20*bl* on the lateral one side (L2>L1), the inclination angle of the inclined portion 20*br* on the other side may be more moderate than the inclination angle of the inclined portion 20*bl* on the one side.

A plurality of elastic strings 23 form an elastic region X, improving the fit of the diaper 1. Specifically, in the upper end portion of the back waist portion 20, a plurality of the elastic strings 23 are continuous from the lateral end 20*el* on the lateral one side to the lateral end 20*er* on the lateral other side, and are arranged side-by-side at a predetermined longitudinal interval. Here, in the longitudinal central portion and the lower longitudinal end portion of the back waist portion 20, the back waist portion 20 is overlapped with the absorbent body 11. In that region, in the lateral central portion of the back waist portion 20, in which the absorbent body 11 is provided, the plurality of elastic strings 23 are not provided. On the other hand, in the region located laterally left (one side) with respect to the absorbent body 11 and in the region located laterally right (other side) with respect to the absorbent body 11, a plurality of the elastic strings 23 are provided substantially parallel with one another.

As shown in FIG. 4, the elastic region X is the region where a plurality of the elastic strings 23 are provided, and extends from the laterally inward end (on the other side) of the first joining region 20*j* to the laterally inward end (on the one side) of the second joining region 40*j*; as mentioned above, the first joining region 20*j* is provided on the lateral one side of the back waist portion 20, and the second joining region 40*j* is provided on the lateral other side. In FIG. 4, the elastic region X is indicated by the hatched portion. Note that for convenience in FIG. 4, hatching has been omitted for the first joining region 20*j* and the second joining region 40*j*.

As shown in FIGS. 2 and 4, a plurality of the elastic strings 23 extend to lateral ends 20*er* and 20*el* of the back waist portion 20. But, providing the first joining region 20*j* and the second joining region 40*j* respectively in these lateral end portions of the back waist portion 20 makes it substantially impossible to exhibit stretching force of the following regions: the first joining region 20*j*; the portion laterally outward of the first joining region 20*j*; the second joining region 40*j*; and the portion laterally outward of the second joining region 40*j*. Accordingly, the lateral range of the elastic region X is from the laterally inward end of the first joining region 20*j* to the laterally inward end of the second joining region 40*j*.

A lateral one-side end Xe1 of the elastic region X is at the same position as the laterally inward end of the first joining region 20*j*, and a lateral other-side end Xe2 of the elastic region X is at the same position as the laterally inward end of the second joining region 40*j*. Note that, in some case, a plurality of elastic strings 23 are also provided in a region (a non-elastic region) other than the elastic region X indicated by the hatched portion in FIG. 4, and the elastic strings 23 are cut in the non-elastic region to prevent stretching force from being exhibited.

In the present embodiment, the lateral center of the absorbent main body 10 (the center line AC) is at the same position as the lateral center of the back waist portion 20. As shown in FIG. 4, in the elastic region X, the distance L3 from the lateral one-side end Xe1 to the center line AC is equal to the distance L4 from the lateral other-side end Xe2 to the center line AC (L3=L4). Note that it is not necessary that the distance L3 from the lateral one-side end Xe1 to the center line AC is equal to the distance L4 from the lateral other-side end Xe2 to the center line AC. Another example will be described later.

Fastening Member 40

The fastening member 40, as shown in FIG. 3C, includes: a skin-side member 401 that is located on the wearer's skin side; a non-skin-side member 402 that is located on the non-skin side; and the fastening portion 41 that is located on the skin side relative to the skin-side member 401 and the non-skin-side member 402. The non-skin-side member 402 has an upper end portion folded back toward the skin side and the upper end portion wraps the upper end portion of the skin-side member 401. As shown in FIG. 2, the fastening member 40 includes a first edge portion 40*a* and a second edge portion 40*b* opposite to the first edge portion 40*a* in the lateral direction. The second edge portion 40*b* of the fastening member 40 is joined to the second joining region 40*j* of the back waist portion 20 by certain joining means (e.g., heat welding or ultrasonic welding), forming the second joining portion 2*b* of the diaper 1.

The skin-side member 401 and the non-skin-side member 402 are each a flexible sheet member that is constituted by a nonwoven fabric or the like. The fastening portion 41 is a hook-and-loop fastener made of polypropylene, etc. and having a plurality of fastening projections (omitted in the drawings) on its skin-side surface. The fastening projections of the fastening portion 41 are hooked to the target region 34 (to be described later) provided in the front waist portion 30, fastening the fastening member 40 to the front waist portion 30.

The second joining portion 2b (the second joining region 40j) is provided extending along the longitudinal direction. The longitudinal length H2 thereof is larger than half the longitudinal length H1 of the lateral end 20er of the back waist portion 20 on the lateral other side (H2>H1/2).

Front Waist Portion 30

The front waist portion 30, as shown in FIG. 3A, includes: a skin-side member 31 that is located on the wearer's skin side; a non-skin-side member 32 that is located on the non-skin side; and a plurality of elastic strings 33 that are located between the skin-side member 31 and the non-skin-side member 32. The non-skin-side member 22 has an upper end portion which is folded back toward the skin side, and the upper end portion wraps the upper end portion of the skin-side member 31 and the upper end portion of the absorbent main body 10. The end portion of the front waist portion 30 on the lateral one side (left) has the joining region 30j, and the joining region 30j is joined to the first joining region 20j of the back waist portion 20, forming the first joining portion 1b.

The skin-side member 31 and the non-skin-side member 32 are each a flexible sheet member that is constituted by a nonwoven fabric or the like. The elastic strings 33 are elastic members that give the front waist portion 30 lateral stretchability. In the present embodiment, a plurality of elastic strings 33 are arranged side-by-side at a predetermined longitudinal interval. And, the elastic strings 33 are joined with an adhesive between the skin-side member 31 and the non-skin-side member 32, with being stretched in the lateral direction.

On the non-skin-side surface of the front waist portion 30, the target region 34 capable of engaging with the fastening portion 41 is provided. For example, the target region 34 is made of a member whose fibers on the upper surface of nonwoven fabric are formed into loop shapes so as to be readily engaged with the fastening projections (hooks) of the fastening portion 41. Note that the following configuration is also acceptable: instead of making the target region 34 and the front waist portion 30 different, the target region 34 is formed by processing a partial region of the non-skin-side member 32 of the front waist portion 30.

The plurality of elastic strings 33 form an elastic region Y, improving the fit of the diaper 1. The plurality of elastic strings 33 extend from the lateral end 30el of the front waist portion 30 on the lateral one side (left) to a predetermined lateral position that is located on the one side relative to the center line AC. In contrast, a plurality of elastic strings 33 are not provided in the range from the lateral end 30er of the front waist portion 30 on the lateral other side (right) to the center line AC. Also, as shown by a hatched portion in FIG. 4, the elastic region Y is a region in which the plurality of elastic strings 33 are provided from the laterally inward, lateral end of the joining region 30j to a position that is located on the laterally one side (left) relative to the lateral one-side end 34el of the target region 34.

Note that, in some case, a plurality of elastic strings 33 are also provided in a region (a non-elastic region) other than the elastic region Y indicated by the hatched portion in FIG. 4, and the elastic strings 33 are cut in the non-elastic region to prevent stretching force from being exhibited.

As shown in FIG. 2, the distance L6 from the center line AC (the lateral center of the absorbent main body 10) to the lateral end 30er of the front waist portion 30 on the lateral other side is smaller than the distance L5 from the center line AC to the lateral end 30el of the front waist portion 30 on the lateral one side (L6<L5).

The distance L6 of the front waist portion 30 on the other side is smaller than the distance L8 from the center line AC to the lateral end 20er of the back waist portion 20 on the lateral other side (L6<L8). In the back waist portion 20, the distance L7 from the center line AC to the lateral end 20el on the lateral one side is equal to the distance L8 from the center line AC to the lateral end 20er on the lateral other side (L7=L8). The lateral position of the lateral end 30el of the front waist portion 30 on the lateral one side is substantially the same as the lateral position of the lateral end 20el of the back waist portion 20 on the lateral one side. Accordingly, the distance L5 from the center line AC to the lateral end 30el of the front waist portion 30 on the lateral one side is equal to the distance L7 from the center line AC to the lateral end 20el of the back waist portion 20 on the lateral one side (L5=L7). From the relations between these distances L5, L6, L7 and L8, the lateral length of the front waist portion 30 is smaller than the lateral length of the back waist portion 20. The lateral end 30er of the front waist portion 30 on the other side is provided laterally inside relative to the other-side, lateral end 20er of the back waist portion 20.

Further, the distance L6 from the lateral end 30er of the front waist portion 30 on the lateral other side to the center line AC is larger than the lateral length L9 of the fastening member 40 (L6>L9). Note that the foregoing relation between lateral distances (lateral lengths) L5, L6, L7, L8 and L9 is present in a state where the front waist portion 30 and the back waist portion 20 are stretched in the lateral direction. This "stretching" state is a state where the back waist portion 20 and the front waist portion 30 are stretched in the lateral direction without creases. More specifically, it is a state as follow: the back waist portion 20 is stretched in the lateral direction such that the lateral dimension thereof is a length equal or close to the lateral dimension of the skin-side member 21 and the lateral dimension of the non-skin-side member 22; and the front waist portion 30 is stretched in the lateral direction such that the lateral dimension thereof is a length equal or close to the lateral dimension of the skin-side member 31 and the lateral dimension of the non-skin-side member 32.

Use and Wearing of Diaper 1

Next, a manner in which the diaper 1 is used and a state where the diaper 1 is put on will be described below with reference to FIGS. 5 to 9.

Figure 6:
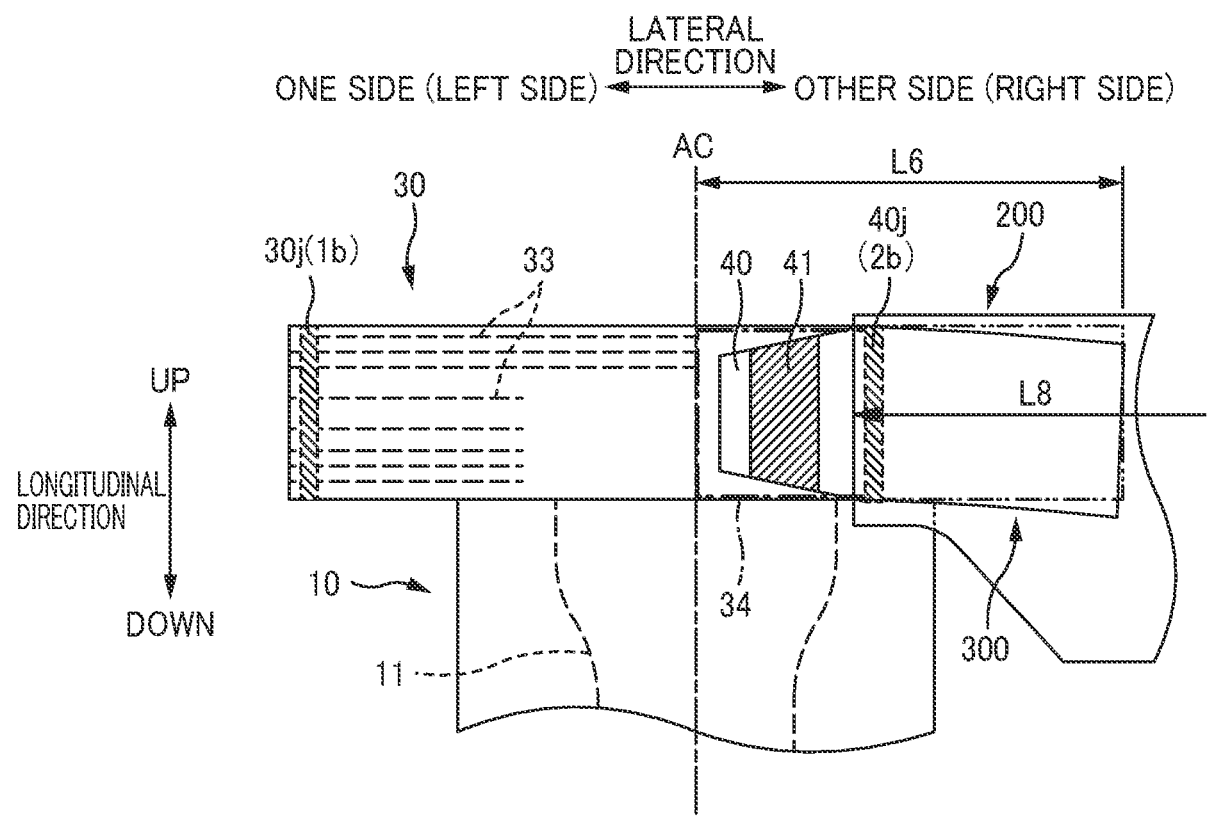
Figure 7A:
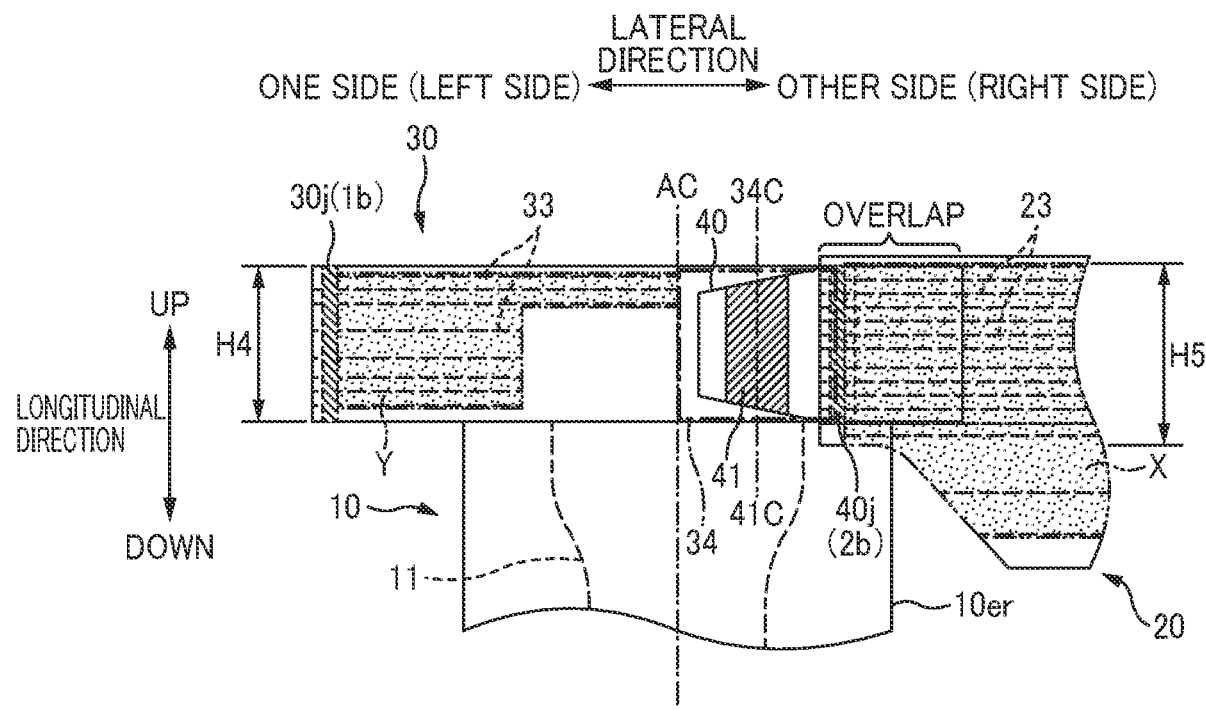
Figure 7B:
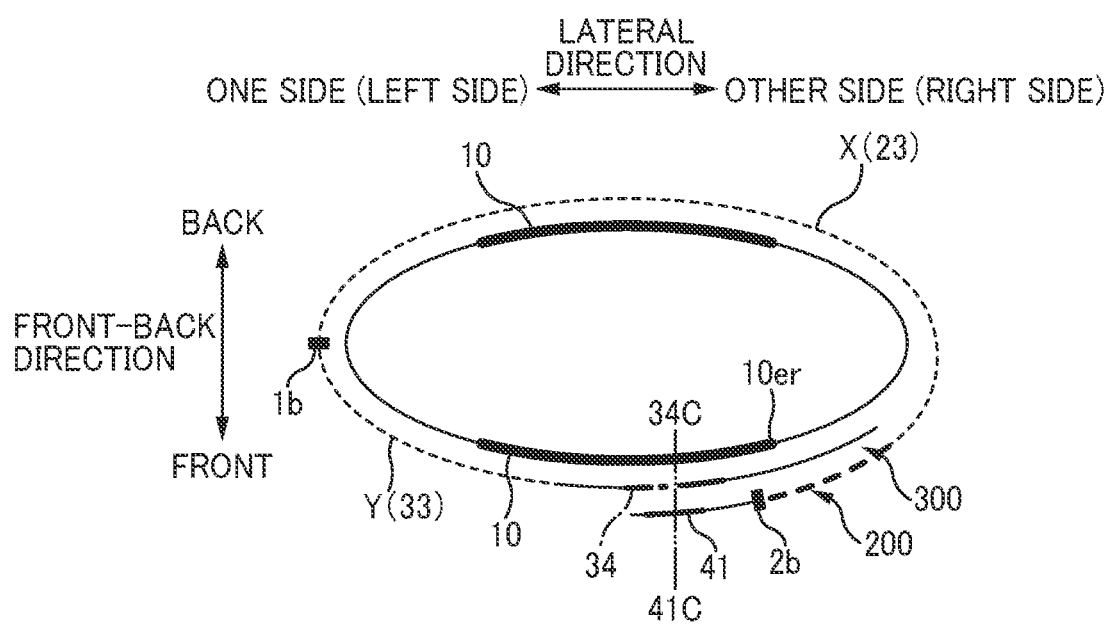
FIG. 7B is a schematic top view of a diaper in FIG. 7A.
Figure 8:
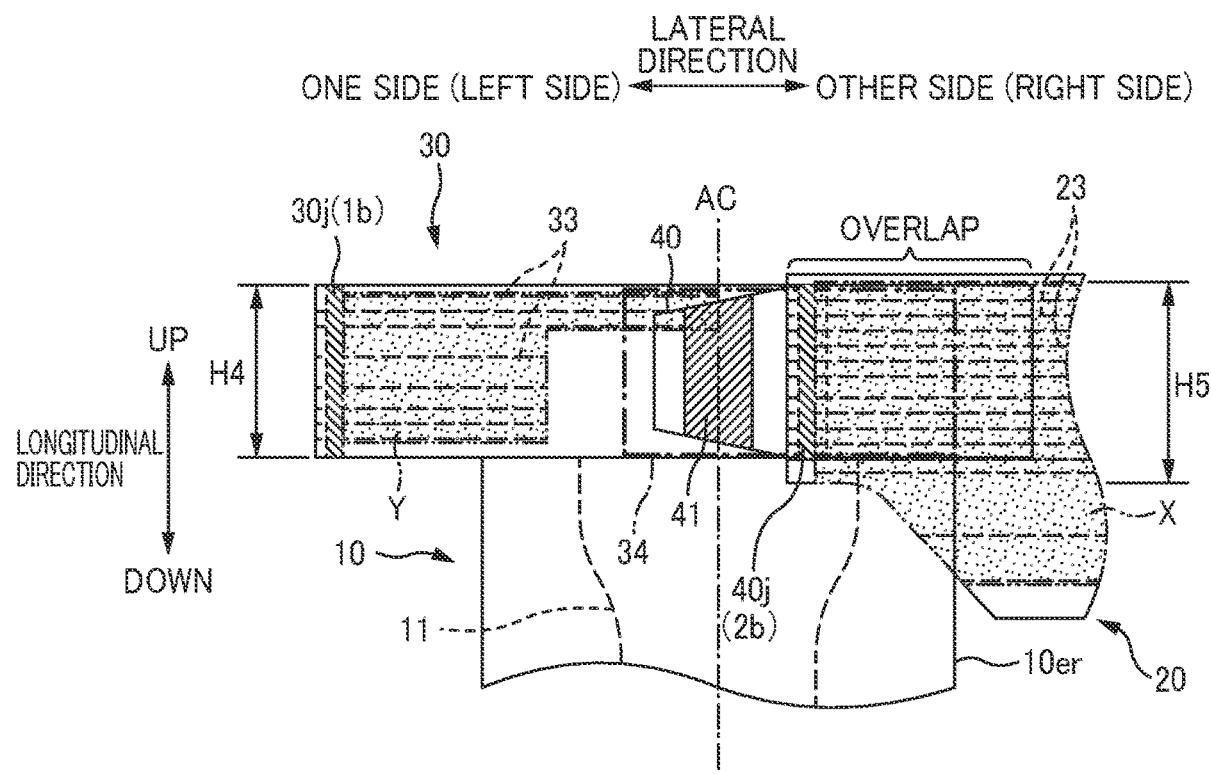
Figure 9A:
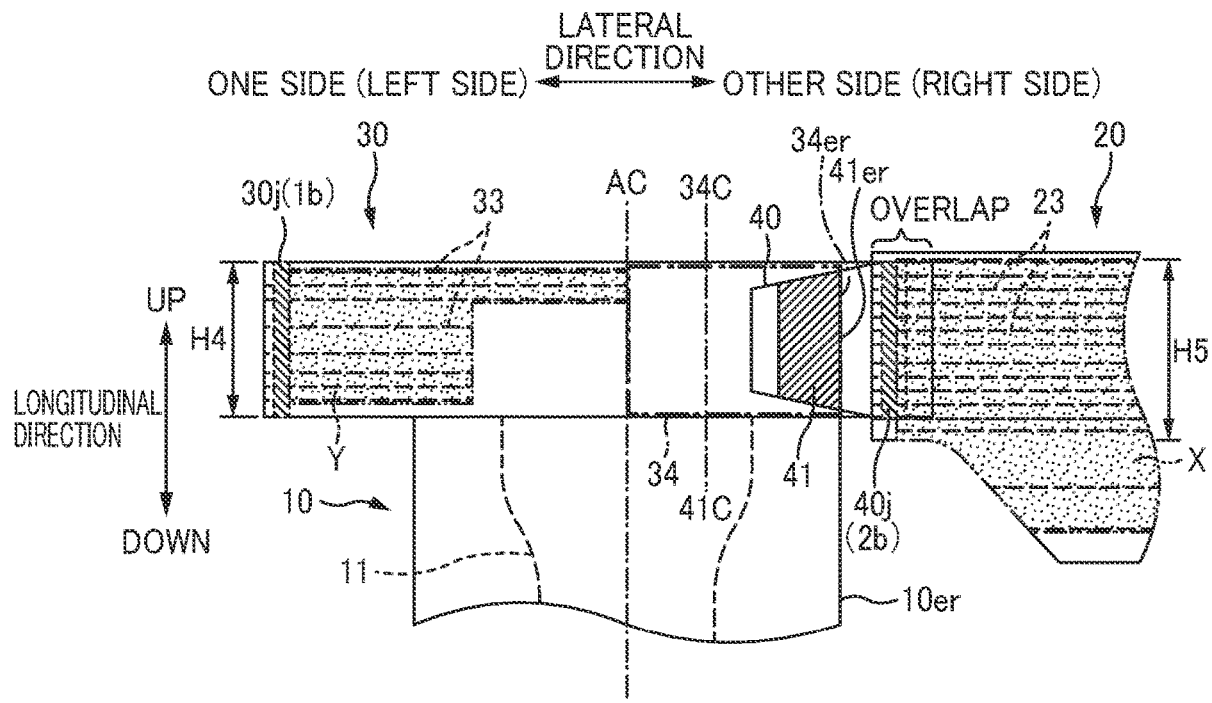
FIG. 9A is a schematic plan view showing a modified example 2 of the range of the target region and the position of a fastening portion when a diaper is put on, and FIG. 9B is a schematic top view of a diaper in FIG. 9A.
Figure 9B:
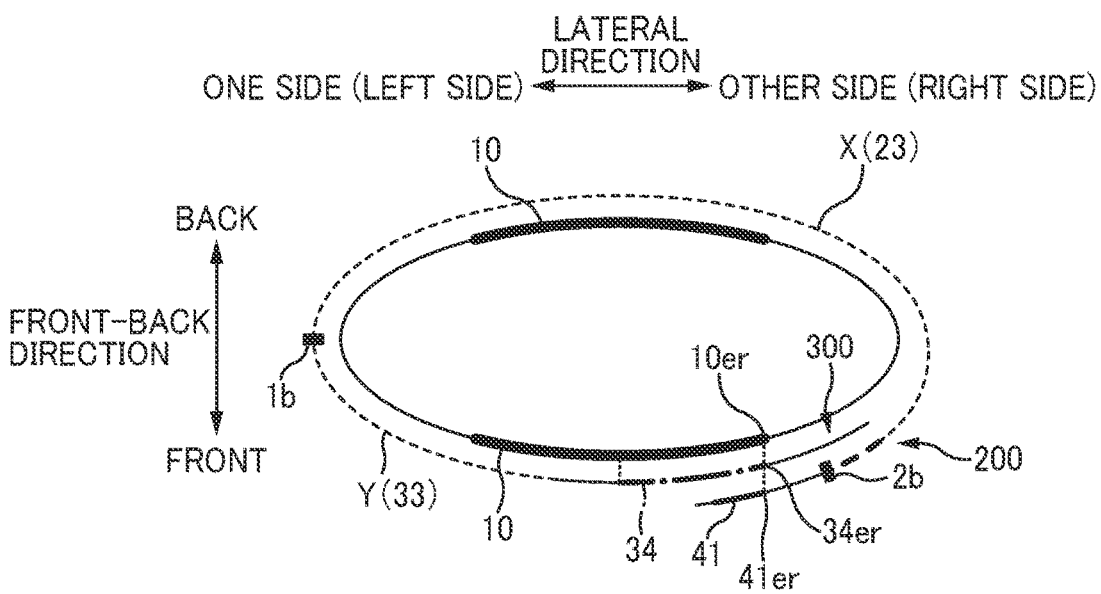

FIG. 5A is a diagram showing a manner in which a diaper is used, FIG. 5B is a side view of a diaper 1 when it is put on, and FIG. 5C is a front view of a diaper 1 when it is put on. FIG. 6 is a diagram illustrating a state where the fastening portion 41 is fastened to the front waist portion 30 when a diaper according to the modified example is put on. FIG. 7A is a schematic plan view showing an example of the range of the target region 34 and the position of the fastening portion 41 when a diaper is put on. FIG. 7B is a schematic top view of the diaper 1 in FIG. 7A. FIG. 8 is a schematic plan view showing a modified example 1 of the range of the target region 34 and the position of the fastening portion 41 when a diaper is put on. FIG. 9A is a schematic plan view showing a modified example 2 of the range of the target region 34 and the position of the fastening portion 41 when a diaper is put on. FIG. 9B is a schematic top view of the diaper 1 in FIG. 9A.

As shown in FIG. 5A, in the laterally one-side end portion of the diaper 1, the front waist portion 30 and the back waist portion 20 are joined together by the first joining portion 1b, thus forming the leg opening 1HL. In contrast, the laterally, other-side end portion is in an open state in which the front waist portion 30 and the back waist portion 20 are not joined together. In other words, the diaper 1 is in a state where its lateral one side is open.

When this diaper 1 is to be put on the wearer (an infant or the like), first, one leg (the right leg) of the wearer is inserted into the leg opening 1HL formed on the one side in the lateral direction of the diaper 1. Then, the leg opening 1HL on the one side is arranged at the joint of the right leg of the wearer, that is to say at the same position as the one leg in the worn state. Thereafter, the operator putting on the diaper pulls the other-side end portion of the front waist portion 30 toward laterally the other side by his/her hand, and then holds it in that state. The operator then pulls the fastening member 40 (the other-side end portion of the back waist portion 20) toward laterally the other side by his/her other hand (indicated by an arrow in FIG. 5A), and wraps it around to the front side of the front waist portion 30. Then, the operator fastens the fastening portion 41 to the target region 34 of the front waist portion 30. Thus, the leg opening 1HL on the other side and the waist opening 1HB are formed, putting the diaper 1 on the wearer (see FIG. 5C).

With this putting-on method, the fastening portion 41 is fastened to the target region 34 while the one of the wearer's legs has been inserted through the leg opening 1HL on the one side, thus making it possible to form the leg opening 1HL on the other side and the waist opening 1HB at the same time. This makes it possible to put on the diaper 1 easily even if the wearer (a newborn infant or an infant) is wriggling their legs.

In the present embodiment, the region of the front waist portion 30 from the lateral one-side end portion to the center line AC includes the elastic region Y extending along the lateral direction; and the region of the front waist portion 30 from the other-side end portion to the center line AC does not include an elastic region (not stretchable). This improves the fit of the diaper 1. The region of the front waist portion 30 from the other-side end portion to the center line AC is a region to which the fastening portion 41 of the fastening member 40 is fastened. Accordingly, there is a possibility that, if elastic members (e.g., the elastic strings 33) are arranged in this region, stretching/contraction of the elastic members makes it easier to remove the foregoing fastening. In order to reduce this problem, no elastic region is provided in the region from the other-side end portion to the center line AC, that is, in the region to which the fastening portion 41 is fastened. In this case, the target region 34 is arranged in a part of the front waist portion 30 in which no elastic region exists.

Further, in the present embodiment, the lateral distance L5 between the center line AC and the one side end of the longitudinal upper end of the front waist portion 30 is larger than the lateral distance L6 between the center line AC and the other-side end of the longitudinal upper end of the front waist portion 30 (L5>L6). This can make smaller a region of the front waist portion 30 on which the back waist portion 20 is stacked in the front-back direction when the fastening portion 41 located on the other side is fastened to the front waist portion 30. This makes it possible to reduce discomfort caused by stacking the back waist portion 20 and the front waist portion 30 when the wearer puts on the diaper.

In the diaper 1, a part of the front waist portion 30 on the other side relative to the center line AC is fastened by the fastening portion 41, and therefore the elastic string 33 is not provided in the part. Even if there are elastic strings 33 in this region, there is a possibility that stretchability deteriorates due to fastening by the fastening portion 41, lowering the stretchability of the part on the other side during a period when putting on the diaper 1, compared to a part on the one side. Accordingly, in the elastic region X of the back waist portion 20 in which a plurality of elastic strings 33 are provided, it is preferable that the number of the elastic strings 33 between the other-side end Xe2 and the center line AC is larger than the number of the elastic strings 33 between the one-side end Xe1 and the center line AC. This makes it possible to improve the fit of the diaper 1.

Further, in the present embodiment, the back waist portion 20 includes the fastening member 40 having the fastening portion 41, and the fastening member 40 is fixed to the other-side end portion of the back waist portion 20, in the second joining region 40j of the back waist portion 20. Making the longitudinal length H2 of the second joining region 40j is set equal to or larger than half the length H1 of the lateral end 20er of the back waist portion 20 on the other side (H2>H1/2). Accordingly, when the fastening member 40 is pulled from the state of FIG. 5A, and is fastened to the front waist portion 30, it is possible to give the force of pulling the fastening member 40 to a not-less-than-half part of the lateral end 20er of the waist portion 20 on the other side. This makes it possible to apply more evenly-distributed force to the front waist portion 30, reducing a possibility of break and deformation of the front waist portion 30, which will be caused by applying excessive force to a part of the front waist portion 30.

Further, the following configuration may be employed: the back waist portion 20, the front waist portion 30 and the absorbent main body 10 are individual components; in the back waist portion 20, on the lateral one side of the lower end portion, the inclined portion 20bl is provided; on the lateral other side of the lower end portion, the inclined portion 20br is provided; and the lateral length L1 of the inclined portion 20bl is larger than the lateral length L2 of the inclined portion 20br (L2>L1). The lateral length L1 of the inclined portion 20bl on the one side is set to a length according to the size of the circumference of a wearer's leg, improving the fit of the leg opening 1HL on the one side to a wearer's leg. And, the lateral length L2 of the inclined portion 20br on the other side may be larger than the lateral length L1 of the inclined portion 20bl on the one side, adjusting the size of the leg opening 1HB on the other side by fastening by the fastening portion 41 when putting on the diaper.

Positional Shift of Stacking Part in which Front Waist Portion 30 and Back Waist Portion 20 are Stacked Next, concerning an other-side end portion 300 of the front waist portion 30 on the other side in the lateral direction and an other-side end portion 200 of the back waist portion 20 on the other side in the lateral direction, positional shift of a stacking part in which the other-side end portion 300 and the other-side end portion 200 will be described below with reference to FIG. 6.

FIG. 6 is a diagram illustrating a state where a diaper according to the modified example is put on.

In the diaper shown in FIG. 6, while the front waist portion 30 and the back waist portion 20 being stretched in the lateral direction, the distance L6 of the front waist portion 30 from the lateral center of the absorbent main body 10 (the center line AC) to the lateral end 30*er* on the other side is equal to or larger than the distance L8 of the back waist portion 20 from the lateral center of the absorbent main body 10 (the center line AC) to the lateral end 20*er* on the other side (L6≥L8; see FIG. 2). In this case, when a diaper is put on, the overlapping part in which the lateral other-side end portion 300 of the front waist portion 30 overlaps the back waist portion 20 on the other side in the lateral direction increases.

In a half-open, underpants-shaped diaper, on the lateral other side (open side), only the fastening portion 41 is fastened to the target region 34 of the front waist portion 30. Accordingly, a part of the front waist portion 30 on the lateral other side relative to the fastening portion (a part in which the front waist portion 30 is stacked on the lateral end portion of the back waist portion 20) is not fixed to the back waist portion 20. For example, concerning a skin-side part of the front waist portion 30 on the lateral other side which overlaps the lateral other-side end portion 200 of the back waist portion 20 (a region including the end portion 300), in a case where a sleeping baby (a wearer) is wriggling his/her legs, the skin-side overlapping part of the front waist portion 30 follows the movement of the baby's legs and is kinked, making longitudinal positional shift easier to occur (see FIG. 6). Also, in a case where a sleeping baby moves (e.g., rolls over) in the lateral direction, the lateral other-side end portion 300 of the front waist portion 30 is likely to rolls toward the one side in the lateral direction. On the other side of the front waist portion 30 in the lateral direction, the larger the part overlapping the lateral other-side end portion of the back waist portion 20 is, the more the foregoing positional shift is likely to occur in the overlapping part. This increases the magnitude of the positional shift. In FIG. 6, the state (the position) of the front waist portion 30 before positional shift is indicated by double dotted/dashed lines.

However, in the diaper 1, as mentioned above, while the front waist portion 30 and the back waist portion 20 being stretched in the lateral direction, the distance L6 of the front waist portion 30 from the lateral center of the absorbent main body 10 (the center line AC) to the lateral end 30*er* on the other side is smaller than the distance L8 of the back waist portion 20 from the lateral center of the absorbent main body 10 (the center line AC) to the lateral end 20*er* on the other side (L6<L8; see FIG. 2). This makes smaller a stacking region of the back waist portion 20 on the laterally other side on which the lateral other-side end portion 300 of the front waist portion 30 is stacked when the diaper 1 is put on. This makes the foregoing positional shift less likely to occur, and even if positional shift occurs, it is possible to reduce the shift. This makes it possible to achieve good fit of the diaper 1 when the diaper 1 is put on.

Next, the position of fastening the fastening portion 41, and the positions of the elastic region X and the second joining portion 2*b* in the fastening state (when a diaper is put on) will be described below with reference to FIGS. 5 to 9.

Fastening Position of Fastening Portion 41

First, the position of fastening the fastening portion 41 will be described below.

In FIGS. 7A and 7B, when the diaper 1 is put on a wearer, the fastening portion 41 is fastened to the front waist portion 30 so that the lateral center 41C of the fastening portion 41 is aligned with the lateral center 34C of the target region 34.

FIG. 8 shows a state in which the fastening portion 41 is fastened so that the waist opening 1HB narrows, compared to the case shown in FIGS. 7A and 7B. Providing the target region 34 in a region on the one side relative to the center line AC makes it possible to fasten the fastening portion 41 to a position located on the one side relative to the center line AC. This increases the overlapping part of the back waist portion 20 and the front waist portion 30, and therefore it is possible to decrease the size of the waist opening 1HB. This makes it possible to give good fit to a wearer (e.g., an infant) whose waist size is small.

In FIGS. 7 to 9, the fastening portion 41 is located so that the entire region thereof overlaps the target region 34. It is not necessary for the entire region of the fastening portion 41 to overlap the target region 34 when fastening. It is sufficient that at least apart of the region overlaps. However, the larger the area of the overlapping part in which the fastening portion 41 overlaps the target region 34, the stronger the fastening of the fastening portion 41 and the target region 34. Accordingly, it is preferable that the entire region of the fastening portion 41 overlaps the target region 34.

FIGS. 9A and 9B are, opposite to FIG. 8, shows a state in which the fastening portion 41 is fastened so that the waist opening 1HB enlarges. In FIGS. 9A and 9B, the fastening portion 41 is fastened to the front waist portion 30 so that the end 41*er* of the fastening portion 41 on the side closer to the second joining portion 2*b* is positioned in the lateral direction on the lateral end 10*er* of the absorbent main body 10 on the lateral other side (the side opposite to the first joining portion 1*b*). This decreases the overlapping part of the back waist portion 20 and the front waist portion 30, and therefore it is possible to increase the size of the waist opening 1HB. This makes it possible to give good fit to a wearer (e.g., an infant) whose waist size is large.

However, when the position of fastening shown in FIGS. 9A and 9B is the reference position of fastening, it is preferable that the fastening portion 41 is fastened to the front waist portion 30 so that the end 41*er* of the fastening portion 41 on the side closer to the second joining portion 2*b* is positioned at the reference position of fastening or positioned laterally inside the reference position of fastening. For example, assuming that the fastening portion 41 is fastened to the front waist portion 30 with the fastening portion 41 projecting from the lower end of the front waist portion 30. In this case, if the end 41*er* of the fastening portion 41 on the side closer to the second joining portion 2*b* is positioned laterally outside the lateral end 10*er* of the absorbent main body 10 on the lateral other side, there is a possibility that a projecting part of the fastening portion 41 having a rigidity comes into contact with a wearer's leg and hurts the wearer's skin. On the other hand, if, as mentioned above, the end 41*er* of the fastening portion 41 on the side closer to the second joining portion 2*b* is positioned at the reference position of fastening or positioned laterally inside the reference position of fastening, the projecting part of the fastening portion 41 is placed on the absorbent main body 10. This makes it possible to prevent the projecting part from coming into contact with a wearer's leg.

As shown in FIGS. 8, 9A and 9B, it is not necessary for the fastening portion 41 to be fastened to the front waist portion 30 so that the lateral center 41C of the fastening portion 41 is aligned with the lateral center 34C of the target region 34.

Position of Elastic Region X when Fastening

Next, the position of the elastic region X when the fastening portion 41 is fastened to the front waist portion 30 (when the diaper 1 is put on) will be described below.

As shown in FIGS. 9A and 9B, when the fastening portion 41 is fastened at the reference position of fastening, the elastic region X is located on the non-skin side of the lateral other-side end portion 300 of the front waist portion 30. And, the elastic region X has a stacking part in which the elastic region X is stacked on the lateral other-side end portion 300 of the front waist portion 30 (indicated by a thick dashed line in FIG. 9B). Note that, when the fastening portion 41 is fastened at a position laterally inside the reference position of fastening (see FIGS. 7A, 7B and. 8), the elastic region X is located on the non-skin side of the lateral other-side end portion 300 of the front waist portion 30, and the elastic region X has a stacking part in which the elastic region X is stacked on the lateral other-side end portion 300 of the front waist portion 30 (indicated by a thick dashed line in FIG. 7B).

As shown in FIG. 6, in a case where the lateral other-side end portion 200 of the back waist portion 20 does not include the elastic region X, when a baby (a wearer) is wriggling his/her legs, or rolling over, the lateral other-side end portion 300 of the front waist portion 30 slides against the lateral other-side end portion 200 of the back waist portion 20, positional shift is more likely to occur in the stacking part, as mentioned above. However, in the diaper 1, the lateral other-side end portion 300 of the front waist portion 30 is pressed against the wearer's skin with the elastic force of the elastic region X. This suppresses positional shift in the stacking part of the front waist portion 30 and the back waist portion 20, making it possible to achieve good fit of the diaper 1 when the diaper 1 is put on.

In the present embodiment, the end portion 300 of the front waist portion 30 on the lateral other side does not have stretchability (the elastic region Y is not included). Accordingly, when the elastic force of the elastic region X is exerted, the lateral other-side end portion 300 of the front waist portion 30 is pressed against the wearer's skin in a surface-to-surface contact manner. This suppresses discomfort of the wearer's skin, improving touch.

In the present embodiment, the longitudinal length H5 of the elastic region X is larger than the longitudinal length H4 of the lateral other-side end portion 300 of the front waist portion 30 (H5>H4). Accordingly, the lateral other-side end portion 300 of the front waist portion 30 can be covered longitudinally with the elastic region X. Consequently, elastic force is exerted on the entire longitudinal region of the lateral other-side end portion 300 of the front waist portion 30, making it possible to further suppress positional shift of the stacking part in which the front waist portion 30 and the back waist portion 20 are stacked.

In the present embodiment, when the fastening portion 41 is fastened at the reference position of fastening (see FIG. 9A) or when the fastening portion 41 is fastened at a position laterally inside the reference position of fastening (see FIGS. 7A and 8), a part of the elastic region X is located on a front side relative to the first joining portion 1b, and the part includes the overlap of the lateral other-side end portion 300 of the front waist portion 30. Accordingly, on the open side of the diaper 1, it is possible to exert elastic force of the elastic region X, improving the fit of the diaper 1.

Position of Second Joining Portion 2b when Fastening

Next, the position of the second joining portion 2b when the fastening portion 41 is fastened to the front waist portion 30 (when the diaper 1 is put on) will be described below.

When the fastening portion 41 is fastened at the reference position of fastening (see FIG. 9A), or when the fastening portion 41 is fastened at a position laterally inside the reference position of fastening (see FIGS. 7A and 8), the second joining portion 2b is located on a front side relative to the first joining portion 1b (see FIGS. 7B and 9B).

A baby (a wearer) usually has a stomach protruding forward, as shown in FIG. 5B, and therefore the front waist portion 30 is subject to downward force by the protrusion of the wearer's stomach (see arrows indicated in FIGS. 5B and 5C). Whereas the joining portion has a rigidity due to the joining of the front waist portion and the back waist portion, the joining portion is usually positioned on the wearer's sides when the diaper is put on. Since the front waist portion is made of soft nonwoven fabric, etc., the front waist portion is likely to slide down, causing positional shift.

However, in the diaper 1, as mentioned above, the second joining portion 2b having a rigidity is located on the front side relative to the first joining portion 1b which is located on the wearer's right side. This makes it possible for the second joining portion 2b to support the protrusion of the wearer's stomach (see FIG. 5C). This suppresses downward positional shift of the front waist portion 30 caused by the protrusion of the wearer's stomach, making better the fit of the diaper 1.

In the present embodiment, the second joining portion 2b is provided along longitudinal direction, in the lateral other-side end portion 200 of the back waist portion 20. The second joining portion 2b has a larger longitudinal length than that in a case where it is provided partially. Accordingly, the second joining portion 2b serves as a "supporting rod" that supports the protrusion of the wearer's stomach, making it possible to further suppress downward positional shift of the front waist portion 30 caused by the protrusion of the wearer's stomach.

In the present embodiment, the number of components stacked in the second joining portion 2b (four) is larger than the number of components stacked in the front waist portion 30 (two) (see FIGS. 3A and 3C). Thus, making the rigidity in the second joining portion 2b larger than the rigidity in the front waist portion 30 enables the protrusion of the wearer's stomach to be supported more securely by the second joining portion 2b. Here, the values of the rigidities of the second joining portion 2b and the front waist portion 30 are exemplified by a value obtained by dividing a measure value of Gurley stiffness by the length of a sample. The Gurley stiffness is measured using a No. 311 Gurley bending stiffness tester of Yasuda Seiki Seisakusho, LTD., according to JIS-L1096.

Note that it is not necessary that the rigidity in the second joining portion 2b is made larger than the rigidity in the front waist portion 30 by making the number of components in the second joining portion 2b larger than the number of components in the front waist portion 30. But, this can make the rigidity larger without taking a measure such as replacing with thicker members, for example.

In the present embodiment, the distance L6 of the front waist portion 30 from the lateral center of the absorbent main body 10 (the center line AC) to the lateral end 30er on the other side is larger than the lateral length L9 of the fastening member 40 (L6>L9; see FIG. 2). Accordingly, when the fastening portion 41 is fastened to the front waist portion 30 so that the lateral tip end of the fastening member 40 (an end opposite to the second joining portion 2b) is positioned on the center line AC, the second joining portion 2b is placed on the end portion 300 of the front waist portion 30 on the lateral other side. Consequently, the second joining portion 2b having a high rigidity does not come into direct contact with wearer's skin. This makes touch better.

In the present embodiment, as shown in FIGS. 7A and 7B, when the fastening portion 41 is fastened to the front waist portion 30 so that the lateral center 41C of the fastening portion 41 is aligned with the lateral center 34C of the target region 34, the second joining portion 2b is located inside the lateral end 10er of the absorbent main body 10 on the lateral other side, and is not positioned on the circumference of a wearer's leg. This makes the second joining portion 2b having a rigidity less likely to come into direct contact with a wearer's leg (skin), making touch better when the diaper 1 is put on.

Modified Example

A modified example of the diaper 1 will be described below with reference to FIGS. 10 and 11. In the diaper 1 according to the modified example, the lateral center of the absorbent main body 10 (the center line AC) is located away laterally from the lateral center of the back waist portion 20 (the center line RC).

Figure 10:
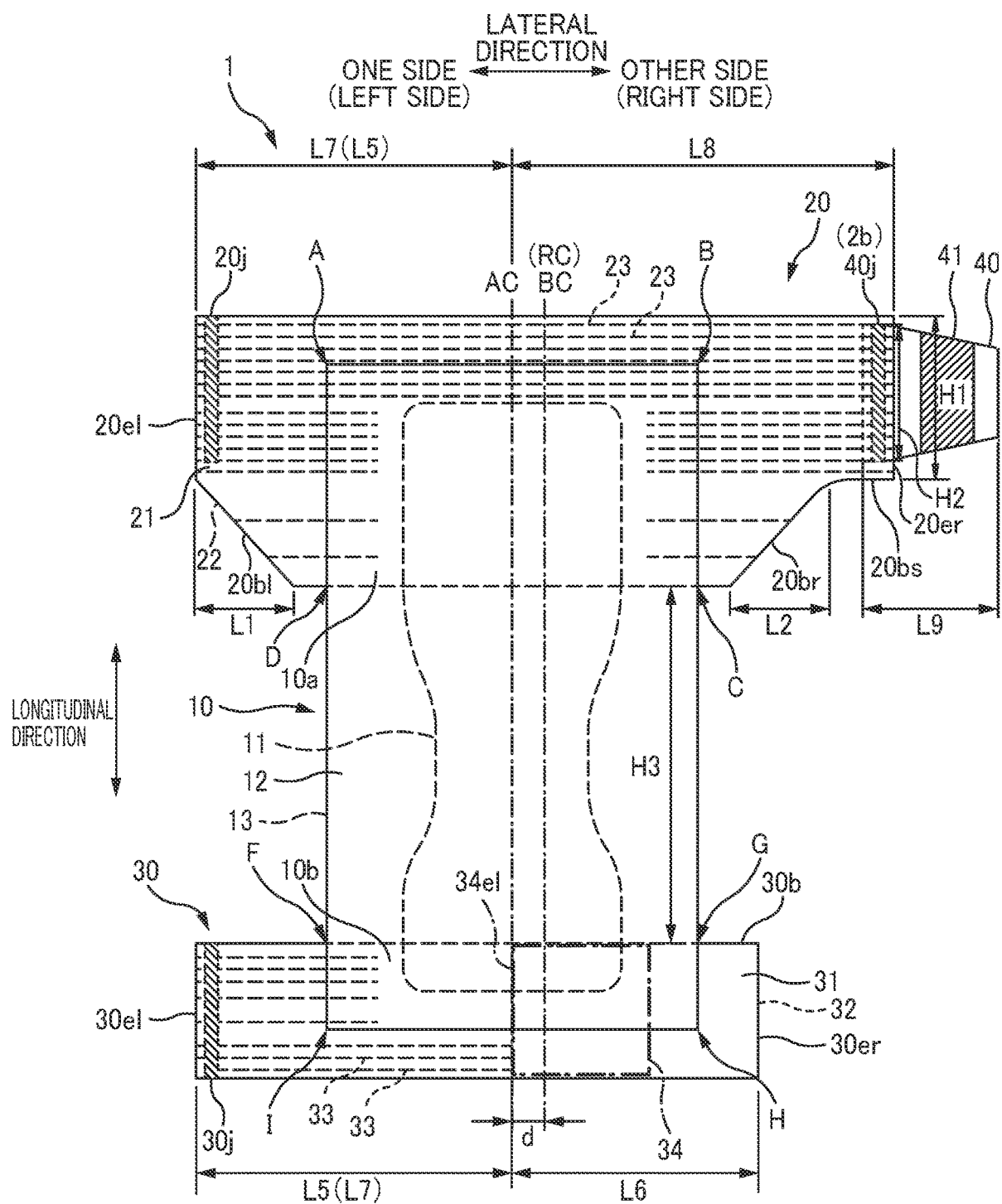
FIG. 10 is a schematic plan view of a diaper according to a modified example in an unfolded state as viewed from the skin side of a wearer.

FIG. 10 is a schematic plan view of a diaper according to a modified example in an unfolded state as viewed from the skin side of a wearer. FIG. 11 is a diagram illustrating the elastic regions X and Y of the diaper 1 according to the modified example.

Figure 11:
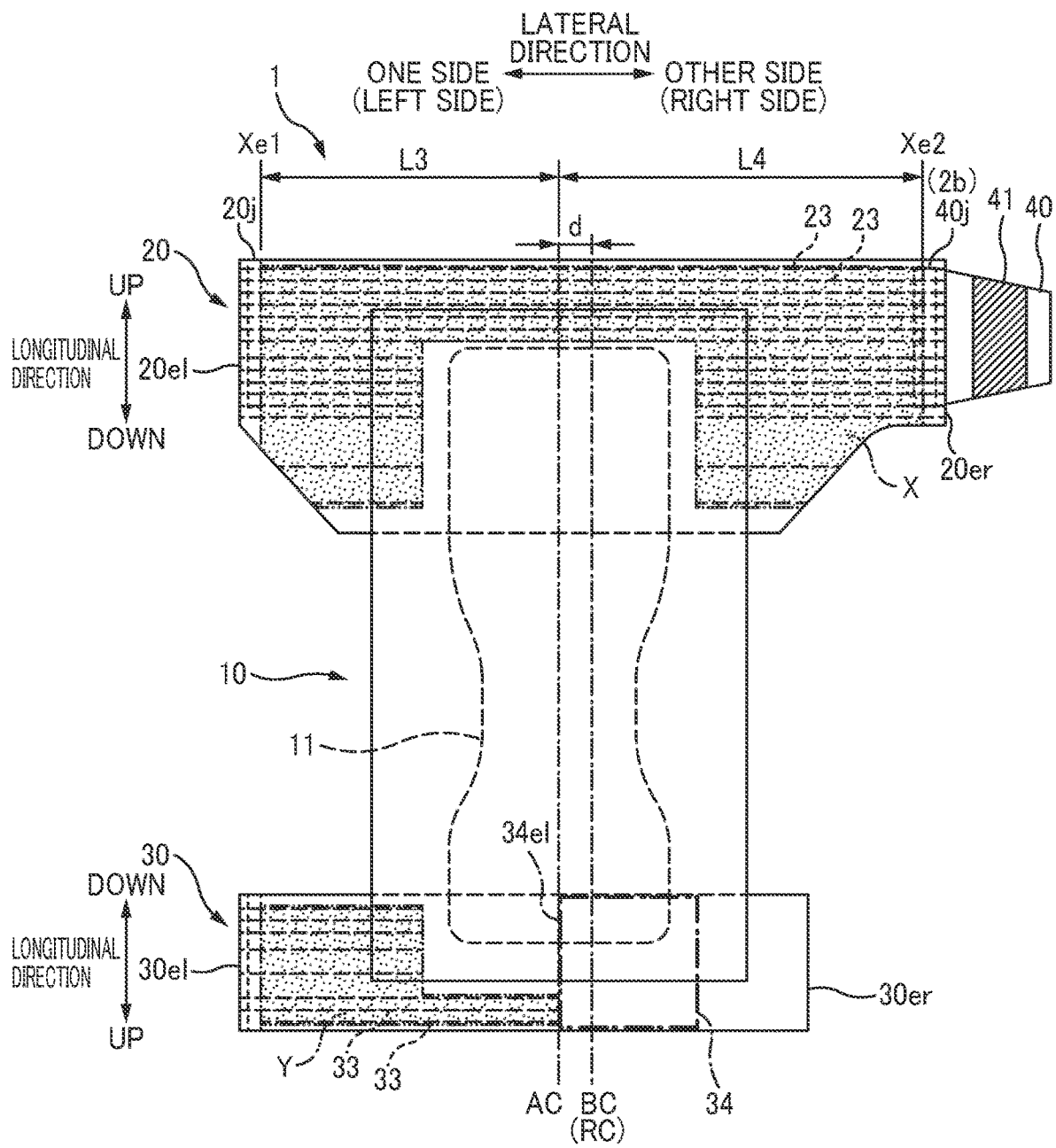
FIG. 11 is a diagram illustrating elastic regions X and Y of a diaper according to the modified example.

In the diaper 1 according to the modified example shown in FIGS. 10 and 11, the lateral center of the back waist portion 20 (the center line RC) is not aligned with the center line AC indicating the lateral center of the absorbent main body 10, and the center line RC is located away laterally at a distance d from the center line AC and on the laterally right side (other side) relative to the center line AC. The lateral center line BC shown in FIGS. 10 and 11 indicates the approximate center of the body of a wearer when a wearer's leg has been inserted. The center line BC is at the same position as the center line RC indicating the lateral center of the back waist portion 20.

Here, the distance d between the center line RC of the back waist portion 20 and the center line AC of the absorbent main body 10 is smaller than the difference between the distance L4 on the lateral other side and the distance L3 on the lateral one side, in the elastic region X as mentioned above (d<L4−L3). More preferably two times the distance d (length 2d) is equal to or less than the difference between the distance L4 on the other side and the distance L3 on the one side (2d≤L4−L3), and most preferably two times the distance d is equal to the difference between the distance L4 on the other side and distance L3 on the one side (2d=L4−L3).

The longitudinal length H1 of the lateral end 20er of the back waist portion 20 on the lateral other side is smaller than half the length H3 from the lower end of the lengthwise, one end portion 10a (the first region) of the absorbent main body 10 to the lower end of the lengthwise, other end portion 10b (the second region) (H1<H3/2).

Assuming that, as in the diaper 1 according to the foregoing embodiment, the distance L3 from the lateral one-side end Xe1 of the elastic region X to the center line AC of the absorbent main body 10 is equal to the distance L4 from the other-side end Xe2 to the center line AC. In this case, the back waist portion 20 is stretched in the lateral direction due to the fastening member 40 being pulled, and therefore the absorbent body 10 will shift on the other side and be displaced from a substantial center of the wearer's body. Consequently, there is a possibility of leakage of excrement, and of wearer's discomfort.

In the diaper 1 according to the modified example, anticipating that the lateral center of the absorbent main body 10 is positioned away from a substantial center of the wearer's body, the elastic region X is formed so that the distance L3 from the lateral one-side end Xe1 to the center line AC of the absorbent main body 10 is smaller than the distance L4 from the lateral other-side end Xe2 to the center line AC (L3<L4). In this case, when the fastening member 40 is pulled to the lateral other side and is fastened to the front waist portion 30, shaping the diaper 1 for putting on, the back waist portion 20 stretches in the lateral direction, and the absorbent main body 10 moves to the lateral other side (to left leg side). And, the center line AC approaches the center line BC, and therefore the absorbent main body 10 can be located closer to the center of the wearer's body.

In the diaper 1 according to the modified example, it is possible for the elastic region X to be formed so that the distance L3 from the lateral one-side end Xe1 to the center line AC of the absorbent main body 10 is different from the distance L4 from the other-side end Xe2 to the center line AC. Accordingly, the distance L3 on the one side is set to a length suitable to the leg opening 1HL according to the size of a leg on the one side (the right leg in the present embodiment), making it possible to improve the fit of the leg opening 1HL on the one side. In addition, fastening by the fastening portion 41 adjusts the leg opening 1HL for a leg on the other side (the left leg in the present embodiment), making it possible to ensure the fit of the leg opening 1HL on the other side.

Further, the lateral distance d from the center line RC of the back waist portion 20 to the center line AC of the absorbent main body 10 is made smaller than the difference between the distance L4 of the elastic region X from the other-side end Xe2 to the center line AC and the distance L3 of the elastic region X from the one-side end Xe1 to the center line AC (d<L4−L3). This can reduce a possibility that, when fastening the fastening portion 41 to the front waist portion 30, the lateral center of the absorbent main body 10 (the center line AC) becomes positioned away from the substantial center of a human body (the center line BC). In the present embodiment, the center line BC indicating the substantial center of a human body is at the same position as the center line RC indicating the lateral center of the back waist portion 20. However, the present invention is not limited thereto. The position of the center line BC may be appropriately adjusted depending on the size of wearer's body, the dimensions of components, the stretching force of elastic members, or the like. And, the position of the center line BC may be different the position of the center line RC.

As mentioned above, the stretching force of the elastic strings 33 does not work in a region of the front waist portion 30 on which the back waist portion 20 and/or the fastening member 40 are stacked. Here, the stretching force of each elastic string 23 is equal to the stretching force of each elastic string 33; and the center line BC indicating the substantial center of a human body is at the same position as the center line RC indicating the lateral center of the back waist portion 20, making two times distance d equal to the difference between the distance L4 and the distance L3 (2d=L4−L3). This configuration realizes the most ideal positional relation allowing the elastic strings 23 and 33 to produce appropriate fit of the waist opening 1HB.

The back waist portion 20, the front waist portion 30 and the absorbent main body 10 are individual components. The absorbent main body 10 has a one end portion 10a on its back side in the front-back direction, and the one end portion 10a is placed on the back waist portion 20. Also, the absorbent main body 10 has an other end portion 10b on its front side in the front-back direction, and the other end portion 10b is placed on the front waist portion 30. the length H1 of a lateral end 20er of the back waist portion 20 on the other side is smaller than half the length H3 of the absorbent main body 10 from the lower end of the one end portion 10a to the lower end of the other end portion 10b (H3/2>H1). Making relatively longer the length H3 of the absorbent main body 10 from the lower end of the one end portion 10a to the lower end of the other end portion 10b makes it possible for the leg openings 1HL to have a length according to the size of the legs. In addition, making shorter the length of the other-side end 20e of the back waist portion 20 makes it easier to transmit to the back waist portion 20 a force of pulling the fastening member 40 when fastening, making it easier to put on the diaper.

In the upper end portion of the back waist portion 20, the elastic region X are laterally continuous at least from the one end of the absorbent main body 10 to the other end, making it possible to reduce a possibility that, when fastening the fastening portion 41 to the front waist portion 30, the lateral center of the absorbent main body 10 (the center line AC) is misaligned with the lateral center of the wearer's crotch (the center line BC).

Others

Although an embodiment of the present invention has been described above, the above embodiment is for facilitating the understanding of the present invention, and is not to be construed as limiting the present invention. The present invention can be modified, improved, etc. without departing from the gist of the present invention, and equivalents of the present invention are also encompassed within the present invention.

Though various configurations are described in the foregoing embodiment, it is sufficient at least that, when the front waist portion 30 and the back waist portion 20 are stretched in the lateral direction, the lateral distance L6 of the front waist portion 30 from the lateral center of the absorbent main body 10 (the center line AC) to the lateral end 30er on the other side is smaller than the lateral distance L8 of the back waist portion 20 from the lateral center of the absorbent main body 10 (the center line AC) to the lateral end 20er on the other side.

In the foregoing embodiment, although the elastic region X for ensuring the fit of the diaper 1 is provided, a configuration is possible in which the elastic region X is provided in only the upper end portion of the back waist portion 20, for example. Even with this configuration, it is possible to ensure a necessary fit for the waist opening 1HB of the diaper 1.

In the foregoing embodiment, the target region 34 are provided in the area of the front waist portion 30 between the lateral center of the absorbent main body 10 (the center line AC) and the lateral end 10er of the absorbent main body 10 on the lateral other side. However, the present invention is not limited thereto. The size of the target region 34 is not particularly limited either as long as the target region 34 is provided so as to satisfy the allowable range of the position at which the fastening portion 41 is fastened (the range inside the lateral end 10er of the absorbent main body 10 on the other side in the lateral direction).

In the foregoing embodiment, the elastic regions X and Y are respectively formed of a plurality of the elastic strings 23 and 33 being capable of stretching/contracting in the lateral direction. However, the present invention is not limited thereto. For example, nonwoven fabric constituting the front waist portion 30 and the back waist portion 20 may be stretchable nonwoven fabric being capable of stretching/contracting in the lateral direction, forming the elastic regions X and Y.

Although the above embodiment illustrates the so-called three piece type of disposable diaper 1 as an example of the absorbent article, there is no limitation whatsoever to this. For example, the absorbent article may be a two piece type of disposable diaper including: a first component is an exterior sheet including a back waist portion and a front waist portion that are connected via a crotch portion as a single unit; and a second component is an absorbent main body that is fixed to the skin-side surface of the exterior sheet.

The foregoing embodiment describes an example in which the target region 34 has loops, the fastening portion 41 has hooks, and the fastening portion 41 is fastened to the target region 34 by the loops becoming caught on the hooks. However, the configurations of the target region 34 and the fastening portion 41 are not limited to the above example. For example, at least one of the target region 34 and the fastening portion 41 may be provided with adhesiveness on its surface, and they may be fastened by adhering this adhesive member to the surface of the other member.

The foregoing embodiment describes the state where the fastening member 40 projects in a lateral direction from the back waist portion 20 when the diaper is put on. However, the fastening member 40 may be folded when the disposable diaper 1 is manufactured, or the fastening member 40 may be provisionally connected to the front waist portion 30 by perforations.

In the foregoing embodiment, although the elastic strings 23 and 33 are not provided in the overlapping regions of the back waist portion 20 and the front waist portion 30 in which they overlap with the absorbent body 11, there is no limitation to this. The elastic strings 23 and 33 may be provided in the regions overlapping with the absorbent body 11. By not providing the elastic strings 23 and 33 in the regions overlapping with the absorbent body 11, it is possible to reduce the risk of the absorbent body 11 deformed due to stretching and contracting of the elastic strings 23 and 33. However, by providing the elastic strings 23 and 33 in the regions overlapping with the absorbent body 11, it is possible to improve the fit of the absorbent main body 10 through stretching force.

The invention claimed is:

1. An absorbent article having a longitudinal direction, a lateral direction intersecting the longitudinal direction, and a front-back direction intersecting the longitudinal direction and the lateral direction, the absorbent article comprising:
    a front waist portion extending along the lateral direction and including first and second end portions on first and second sides respectively in the lateral direction;
    a back waist portion extending along the lateral direction and including first and second end portions on the first and second sides respectively in the lateral direction;
    a crotch portion provided between the front waist portion and the back waist portion; and
    a fastening member joined to the back waist portion, wherein
    each of the front waist portion and the back waist portion includes an elastic region extending along the lateral direction,
    the first end portion of the back waist portion is directly and undetachably joined to the first end portion of the front waist portion to define a first joining portion,
    the second end portion of the back waist portion is joined to the fastening member to define a second joining portion, and is not joined to the second end portion of the front waist portion,
    the fastening member has a fastening portion configured to be fastened to the front waist portion when the absorbent article is worn,
    the fastening member includes a first edge portion and a second edge portion opposite to the first edge portion in the lateral direction and directly joined to the second end portion of the back waist portion, an edge of the second end portion of the back waist portion on the second side is located between the first and second edge portions of the fastening member in the lateral direction, while the front waist portion and the back waist portion are being stretched in the lateral direction, a lateral distance of the front waist portion from a lateral center of the crotch portion to an edge of the second end portion of the front waist portion on the second side in the lateral direction is smaller than a lateral distance of the back waist portion from the lateral center of the crotch portion to the edge of the second end portion of the back waist portion on the second side in the lateral direction, and the lateral distance of the back waist portion from the lateral center of the crotch portion to the edge of the second end portion of the back waist portion on the second side in the lateral direction excludes an entirety of a lateral distance of the fastening member extending outwardly from the edge of the second end portion of the back waist portion on the second side in the lateral direction to an outermost edge of the first edge portion of the fastening member.

2. The absorbent article according to claim 1, wherein while the front waist portion and the back waist portion are being stretched in the lateral direction, the lateral distance of the front waist portion from the lateral center of the crotch portion to the edge of the second end portion of the front waist portion on the second side is larger than a lateral length of the fastening member in the lateral direction.

3. The absorbent article according to claim 1, wherein the elastic region of the back waist portion is arranged in the second end portion of the back waist portion, and while the fastening portion is fastened to the front waist portion so that an end of the fastening portion on a side closer to the second joining portion is positioned in the lateral direction on an end of the crotch portion opposite to the first joining portion, the elastic region arranged in the second end portion of the back waist portion is located on a non-skin side of the second end portion of the front waist portion, and the elastic region arranged in the second end portion of the back waist portion has a stacking part in which the elastic region is stacked on the second end portion of the front waist portion.

4. The absorbent article according to claim 3, wherein the second end portion of the front waist portion does not have stretchability in the lateral direction.

5. The absorbent article according to claim 3, wherein while the fastening portion is fastened to the front waist portion so that the end of the fastening portion on the side closer to the second joining portion is positioned in the lateral direction on the end of the crotch portion opposite to the first joining portion, a longitudinal length, in the longitudinal direction, of the elastic region arranged in the second end portion of the back waist portion is larger than a longitudinal length, in the longitudinal direction, of the second end portion of the front waist portion.

6. The absorbent article according to claim 1, wherein while the fastening portion is fastened to the front waist portion so that an end of the fastening portion on a side closer to the second joining portion is positioned in the lateral direction on an end of the crotch portion opposite to the first joining portion, the second joining portion is located on a front side relative to the first joining portion.

7. The absorbent article according to claim 6, wherein a rigidity of the second joining portion is larger than a rigidity of the front waist portion.

8. The absorbent article according to claim 7, wherein a number of components stacked in the second joining portion is larger than a number of components stacked in the front waist portion.

9. The absorbent article according to claim 1, wherein the second end portion of the back waist portion is directly joined to the fastening member to define the second joining portion, and is not directly joined to the second end portion of the front waist portion.

10. The absorbent article according to claim 1, wherein the back waist portion extends, in the lateral direction, from the edge of the second end portion of the back waist portion on the second side to an edge of the first end portion of the back waist portion on the first side.

* * * * *